US006524567B2

(12) United States Patent
Laub

(10) Patent No.: US 6,524,567 B2
(45) Date of Patent: *Feb. 25, 2003

(54) SYNTHETIC SOIL-EXTRACT MATERIALS AND MEDICAMENTS FOR HEMORRHAGIC FEVER VIRUSES BASED THEREON

(75) Inventor: Richard J. Laub, Newport Beach, CA (US)

(73) Assignee: Laub Biochemicals Corp., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/976,513

(22) Filed: Oct. 11, 2001

(65) Prior Publication Data

US 2002/0049299 A1 Apr. 25, 2002

Related U.S. Application Data

(60) Continuation-in-part of application No. 09/345,865, filed on Jul. 1, 1999, which is a division of application No. 08/798,329, filed on Feb. 10, 1997, now Pat. No. 5,945,446.

(51) Int. Cl.$^7$ .................. A61K 31/74; A61K 39/385; A61K 31/35

(52) U.S. Cl. .................. 424/78.02; 424/195.11; 514/456

(58) Field of Search .................. 424/78.02, 195.11; 514/456

(56) References Cited

U.S. PATENT DOCUMENTS

| 4,921,840 A | 5/1990 | Seubert et al. |
| 4,999,202 A | 3/1991 | Cronje et al. |
| 5,284,651 A | 2/1994 | Riede et al. |

FOREIGN PATENT DOCUMENTS

| DE | 3830333 C1 | 3/1990 |
| DE | 0537430 A1 | 4/1993 |
| DE | 41 34 378 A1 | 4/1993 |
| EP | 0119768 A1 | 9/1984 |
| WO | WO 95/08335 | 3/1995 |

OTHER PUBLICATIONS

HealthGate Document—R. Ansorg et al.—Studies on the Antimicrobial Effect of Natural and Synthetic Humic Acids—*Arzeimittelforschung* 1978, 28(12), pp. 2195–2198.
HealthGate Document—K.D. Thiel et al.—Comparison of the in Vitro Activities of Ammonium Humate and of Enzymically Oxidized Chlorogenic and Caffeic Acids Against Type 1 and Type 2 Human Herpes Virus—*Pharmazie* 1981, 36(1), pp. 50–53.

(List continued on next page.)

*Primary Examiner*—Thurman K. Page
*Assistant Examiner*—Blessing Fubara
(74) *Attorney, Agent, or Firm*—Knobbe, Martens, Olson & Bear, LLP

(57) ABSTRACT

Phenolic polymers are prepared by oxidizing and polymerizing starting organic compounds comprising at least one hydroxyl group and at least one carbonyl group or at least two hydroxyl groups on an aromatic structure. One or more inorganic compounds or salts is added and the solution is allowed to stand at about 20° C. to 80° C. for a period of about at least 2 hours. Salt molecules as well as starting compounds and other low molecular-weight materials below about 500 to about 10,000 daltons are removed from the product solution. Purified phenolic polymers are prepared in concentrated aqueous solution or in dried powder form in a final step if necessary. The resultant phenolic polymers exhibit physicochemical properties strongly resembling those of typical commercially-available natural-product soil extracts. The materials are active hemorrhagic fever antiviral agents, and are effective in anti-viral compositions for treating or preventing hemorrhagic fever viral diseases.

48 Claims, 2 Drawing Sheets

OTHER PUBLICATIONS

HealthGate Document—H. Schultz—Investigations on the Viricidal Effects of Humic Acids in Peat–Mull—*Dtsch Tierarztl Wochenschr* Jul. 1, 1965, 72(13), pp. 294–297.

HealthGate Document—R. Klöcking et al.—Antiviral Properties of Humic Acids—*Experientia* May 15, 1972, 28(5), pp. 607–608 (Article & Abstract).

HealthGate Document—G. Sydow et al.—The Effect of Phenolic Polymers on Retroviruses—*Pharmazie* Dec. 1986, 41(12), pp. 865–868.

HealthGate Document—R. Klöcking et al.—Antiviral Activity of Phenolic Polymers Against Type 1 Herpesvirus Hominis—*Pharmazie* Aug. 1978, 33(8), p. 539.

HealthGate Document—F. Schiller et al.—Results of an Oriented Clinical Trial of Ammonium Humate for the Local Treatment of Herpesvirus Hominus (HVH) Infections—*Dermatol Monatsschr* Jul. 1979, 165(7), pp. 505–509.

HealthGate Document—B. Helbig et al.—Therapeutic Effect of (E)–5–(2–Bromovinyl)–2'–Deoxyuridine, Caffeic Acid Oxidation Product, and Trisodiumphosphonoformate on Cutaneous Herpes Simplex Virus Type 1 Infection in Guinea Pigs—*J. Med Virol* Nov. 1987, 23(3), pp. 303–309.

R. Klöcking—Interaction of Humic Acids and Humic–Acid–Like Polymers with Herpes Simplex Virus Type 1—*Humanic Substances in the Aquatic and Terrestrial Environment*, Berlin 1991, pp. 408–412.

HealthGate Document—In Vitro Studies of the Antiviral Activity of Enzymatically Oxidized O–Diphenolic Compounds Against Herpes Simplex Virus Type 1 and 2—*Zentralbl Bakterios (Orig. A)* Mar. 1979, 234(2), pp. 159–169.

HealthGate Document—K.D. Thiel et al.—In Vitro Studies of the Antiviral Activity of Ammonium Humate Against Herpes Simplex Virus Type 1 and Type 2—*Zentralbl Bakteriol (Orig. A)* Nov. 1977, 239(3), pp. 304–321.

HealthGate Document—K.D. Thiel et al.—Antiviral Activity of Enzymatically Oxidized Caffeic Acid Against Herpesvirus Hominis Type 1 and Type 2—*Acta Virol* May 1983, 27(3), pp. 200–208.

HealthGate Document—K.D. Thiel et al. —Antiviral Effect of Enzymatically and Nonenzymatically Oxidized Caffeic and Hydrocaffeic Acids Against Herpesvirus Hominis Type 1 and Type 2 in Vitro—*Pharmazie* Nov. 1984 39(11), pp. 781–782.

M. Cushman et al.—Preparation and Anti–HIV Activities of Aurintricarboxylic Acid Fractions and Analogues: Direct Correlation of Antiviral Potency with Molecular Weight—*Journal of Medicinal Chemistry* 1991, 34(1), pp. 329–337.

M. Cushman et al.—Synthesis and Anti–HIV Activites of Low Molecular Weight Aurintricarboxylic Acid Fragments and Related Compounds—*Journal of Medicinal Chemistry* 1991, vol. 34, pp. 337–342.

HealthGate Document—D. Schols et al.—(Abstract & article) Selective Inhibitory Activity of Polyhydroxcarboxylates Derived from Phenolic Compounds Against Human Immunodeficiency Virus Replication—*J Acquir Immune Defic Syndr* 1991, 4(7), pp. 677–685.

S. Loya et al.—Hexaprenoid Hydroquinones, Novel Inhibitors of the Reverse Transcriptase of Human Immunodeficiency Virus Type 1—*Journal of Natural Products* Dec. 1993, 56(12), pp. 2120–2125.

J. Schneider et al.—Inhibition of HIV–1 in Cell Culture by Synthetic Humate Analogues Derived from Hydroquinone: Mechanism of Inhibition—*Virology* 1996, 218(2), pp. 389–395.

HealthGate Document—J. Hills et al.—Inhibition of Several Strains of Influenza Virus Type A and B by Phenolic Polymers—*Biomed Biochim Acta* 1986, 45(9), pp. 1173–1179 (including German article).

A. Jankowski et al.—A Randomized, Double–Blind Study on the Efficacy of Tolpa Torf Preparation (TTP) in the Treatment of Recurrent Respiratory Tract Infections—*Arch Immunol Ther Exp (Warsz)* 1993, 41(1), pp. 95–97.

R. Klöcking et al.—TITLE?—*Pharmazie* 1977, 32, p. 297.

HealthGate Document—R. Mentel, et al. "Effectiveness of Phenol Body Polymers Against Influenza Virus A/Krasnodar/101/59H2N2" *Biomed Biochem Acta* 1983 42 (10). pp. 1353–1356.

HealthGate Document—R. Klöcking et al.—Preparation, Characterization and Antiviral Activity of Phenolic Polyers. 2. Antiviral Activity of Phenolic Polymers (Proceedings)—*Pharmazie* May 1979, 34(5–6), pp. 293–294.

HealthGate Document—H.P. Klöcking et al.—Effect of Phenol Ring Polymers on the Release of Plasminogen Activators—*Farmakol Toksikol* Jan.–Feb. 1984, 47(1), pp. 93–95.

K.I. Hanninen et al.—Synthesis and Characterization of Humic Acid–Like Polymers—*The Science of the Total Environment* 1987, 62, pp. 201–210.

HealthGate Document—M. Robert–Gero et al.—Biochemical Study of Humus Action of a Proteolytic Enzyme on Natural and Synthetic Humic Polymers and Those of Microbial Origin—*Ann Inst Pasteur (Paris)* Dec. 1967, 113(6), pp. 903–909.

HealthGate Document—M. Jakubiec et al.—Comparison of the Effect of Natural and Synthetic Humates and EDTA on the Growth of *Escherichia coli* —**Abstract not available.

HealthGate Document—J. Pommery et al.—SOS Chromotest Study Concerning Some Appreciation Criteria of Humic Substances' Genotoxic Potency—*Mutat Res* Jun. 1989, 223(2), pp. 183–189.

HealthGate Document—F.J. Lu, et al., Department of Biochemistry et al.—Humic Acid: Inhibitor of Plasmin—*Sci Total Environ* Apr. 1992, 114, pp. 135–139.

HealthGate Document—K. Wiegleb et al.—The Use of the HET–CAM Test for the Determination of the Irritating Effects of Humic Acids—*DTW Dtsch Tierarztl Wochenschr* Oct. 1993, 100(10), pp. 412–416.

HealthGate Document—W. Seffner—Subchronic Application of Humic Acids and Associated Compounds Provokes Histological Changes of Goitre in the Rat—*Exp Toxicol Pathol* Jan. 1995, 47(1), pp. 63–70.

HealthGate Document—J. Schneider—Inhibition of HIV–1 Cell Culture by Synthetic Humate Analogues Derived from Hydroquinone Mechanism of Inhibition—*Virology* Apr. 15, 1996, 218(2), pp. 389–395.

Hassett et al., "Humic Acids: Synthesis, Properties and Assimilation of Yeast Biomass" *Soil Biol. Biochem*, vol. 20, No. 2 pp. 227–231, 1988.

Shindo, "Catalytic Effect of Volcanic Ash on the Formation of Humic Polymers in Ando Soils" *The Science of the Total Environment*, 117/118 (1992) 93–101.

"Sulfated Polysaccharides Are Potent and Selective Inhibitors of Various Enveloped Viruses, Including Herpes Simplex Virus, Cytomegalovirus, Vesicular Stomatitis Virus, and Human Immunodeficiency Virus"—Masanori Baba, Robert Snoeck, Rudi Pauwels, and Erik De Clercq. Antimicrobial Agents and Chemotherapy, Nov. 1988, p. 1742–1745, vol. 32, No. 11.

Comparison of Core Antigen (p24) Assay and Reverse Transcriptase Activity for Detection of Human Immunodeficiency Virus Type 1 Replication—Sally Land, Fiona Beaton, Dale A. McPhee, and Ian D. Gust, *Journal of Clinical Microbiology*, Mar. 1989, p. 486–489, vol. 27, No. 3.

C. Schewe et al. "Lipoxygenase–Inhibitory Action of Antiviral Polymeric Oxidation Porducts of Polyphenols" *Biomed Biochem Acta* 50 (1991) 3, 299–305.

H.L. Yang, et al., "Humic Acid Induces Expression of Tissue Factor by Cultured Endothelial Cells: Regulation by Cytosolic Calcium and Protein Kinase C," *Thromb Haemost* Mar. 1994. 71 (3). pp. 325–330.

SYNTHETIC SOIL-EXTRACT MATERIALS AND MEDICAMENTS FOR HEMORRHAGIC FEVER VIRUSES BASED THEREON

CROSS-REFERENCE TO RELATED APPLICATION

This application is a continuation-in-part of application Ser. No. 09/345,865, filed Jul. 1, 1999, which is a divisional of application Ser. No. 08/798,329, filed Feb. 10, 1997, now U.S. Pat. No. 5,945,446, issued Aug. 31, 1999.

BACKGROUND OF THE INVENTION

1. Field of the Invention

This invention relates to synthetic soil extract substances comprising phenolic polymers, and to compositions and methods for employing the synthetic phenolic polymers for preventing, reducing, treating, or eliminating hemorrhagic fever viral diseases.

2. Description of the Related Art

Soil extract materials, particularly the classes of substances known collectively as "humus," "humics," "humic acid(s)," or "humates," have been widely used in a number of applications for many years, as reviewed by F. J. Stevenson, *Humus Chemistry. Genesis Composition Reactions;* New York: Wiley, 1964; and, more recently, by A. Piccolo, *Humic Substances in Terrestrial Ecosystems;* New York: Elsevier, 1996.

Humic substances have long been known to exhibit antiviral properties (H. Schultz, *Dtsch. Tierarztl. Wochenschr.* 1962, 69, 613; 1965, 72(13), 294–297; R. Klocking and M. Sprossig, *Experientia* 1972, 28(5), 607–608), particularly retroviruses (G. Sydow, V. Wunderlich, R. Klocking, and B. Helbig, *Pharmazie* 1986, 41(12), 865–868). Viral pathogens for which soil-extract materials have been shown to be effective include in particular Coxsackie virus A9 (Griggs-Baylor) (R. Klocking and M. Sprossig, *Experientia* 1972, 28(5), 607–608), herpes simplex virus type 1 (B. T. Rouse (Ed.), *Herpes Simplex Virus;* Berlin: Springer-Verlag, 1992; R. Klocking, K. D. Thiel, P. Wutzler, B. Helbig, and P. Drabke, *Pharmazie* 1978, 33(8), 539; F. Schiller, R. Klocking, P. Wutzler, and I. Farber, *Dermatol. Monatsschr.* 1979, 165(7), 505–509; B. Helbig, A. Sauerbrei, R. Klocking, P. Wutzler, N. Wicht, U. Wiedemann, and G. Herrmann, *J. Med. Virol.* 1987, 23(3), 303–309; R. Klocking and B. Helbig, in *Humic Substances in the Aquatic and Terrestrial Environment;* Berlin: Springer-Verlag, 1991; 407–412;) and type 2 (anon. *Zentralbl. Bakteriol* [*Orig. A*] 1976, 234(2), 159–169; K. D. Thiel, R. Klocking, H. Schweizer, and M. Sprossig, *Zentralbl. Bakteriol* [*Orig. A*] 1977, 239(3), 304–321; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782); human immunodeficiency virus (HIV) (M. Cushman, P. Wang, S. H. Chang, C. Wild, E. De Clercq, D. Schols, M. E. Goldman, and J. A. Bowen, *J. Med. Chem.* 1991, 34(1), 329–337; M. Cushman, S. Kanamathareddy, E. De Clercq, D. Schols, M. E. Goldman, and J. A. Bowen, *J. Med. Chem.* 1991, 34(1), 337–342; D. Schols, P. Wutzler, R. Klocking, B. Helbig, and E. De Clercq, *J. Acquir. Immune Defic. Syndr.* 1991, 4(7), 677–685; S. Loya, R. Tal, A. Hizi, S. Issacs, Y. Kashman, and Y. Loya, *J. Nat. Prod.* 1993, 56(12), 2120–2125; J. Schneider, R. Weis, C. Manner, B, Kary, A. Werner, B. J. Seubert, and U. N. Riede, *Virology* 1996, 218(2), 389–395; influenza virus type A (Krasnodar/101/59/H2N2) (R. Mentel, B. Helbig, R. Klocking, L. Dohner, and M. Sprossig, *Biomed. Biochim. Acta* 1983, 42(10), 1353–1356); and type B (J. Hils, A. May, M. Sperber, R. Klocking, B. Helbig, and M. Sprossig, *Biomed. Biochim. Acta* 1986, 45(9), 1173–1179); as well as other respiratory tract infectious agents (A. Jankowski, B. Nienartowicz, B. Polanska, and A. Lewandowicz-Uszyuska, *Arch. Immunol. Ther. Exp.* (Warsz) 1993, 41(1), 95–97).

The mechanisms whereby humic substances inhibit the cytopathicity of a number of viruses have been studied in some detail. It is thought that the materials prevent viral replication in part by sorbing onto the viral envelope protein (gp120 in the case of HIV), and thereby block the sorption of viral particles to cell surfaces: K. D. Thiel, R. Klocking, H. Schweizer, and M. Sprossig, *Zentralbl. Bakteriol.* [*Orig. A*] 1977, 239(3), 304–321; D. Schols, P. Wutzler, R. Klocking, B. Helbig, and E. De Clercq, *J. Acquir. Immune Defic. Syndr.* 1991, 4(7), 677–685; anon., *Fortschr. Med.* 1995, 113(7), 10; J. Schneider, R. Weis, C. Manner, B. Kary, A. Werner, B. J. Seubert, and U. N. Riede, *Virology* 1996, 218(2), 389–395. [Extracellular interception of pathogens by chemical agents that bind to them is a well-known means of immunological defense (D. M. Shankel, S. Kuo, C. Haines, and L. A. Mitscher, in *Antimutagenesis and Anticarcinogenesis Mechanisms III;* G. Bronzetti, H. Hayatsu, S. De Flora, M. D. Waters, and D. M. Shankel (Eds.); New York: Plenum, 1993; 65–74). Such materials might well be termed "despathogens", following the terminology proposed by T. Kada and K. Shimoi, *Bioessays* 1987, 7, 113–116, regarding "desmutagens".] It has also been found that naturally-occurring humic acid preparations can stimulate the production of cytokines, including interferon-gamma, interferon-alpha, and tumor necrosis factor-alpha (A. D. Inglot, J. Zielinksa-Jenczylik, and E. Piasecki, *Arch. Immunol. Ther. Exp.* (Warsz) 1993, 41(1), 73–80); as well as interferon-beta (Z. Blach-Olszewska, E. Zaczynksa, E. Broniarek, and A. D. Inglot, *Arch. Immunol. Ther. Exp.* (Warsz), 1993, 41(1), 81–85).

The toxicity of naturally-occurring humic acids is remarkably low (K. D. Thiel, B. Helbig, R. Klocking, P. Wutzler, M. Sprossig, and H. Schweizer, *Pharmazie* 1981, 36(1), 50–53; U. N. Riede, I. Jonas, B. Kirn, U. H. Usener, W. Kreutz, and W. Schlickewey, *Arch. Orthop. Trauma Surg.* 1992, 111(5), 259–264; H. Czyzewska-Szafran, Z. Jastrzebski, D. Soltysiak-Pawluczak, M. Wutkiewicz, A. Jedrych, and M. Remiszewska, *Acta Pol. Pharm.* 1993, 50(4–5), 373–377; H. L. Yang, F. J. Lu, S. L. Wung, and H. C. Chiu, *Thromb. Haemost.* 1994, 71(3), 325–330). [Cytotoxic effects of anti-viral substances, including humic acids, are usually evaluated via biological (viability and alterations of cell morphology) and biochemical testing methods ($^{51}$Cr release), as described by K. D. Thiel, U. Eichhom, H. Schweizer, and R. Klocking, *Arch. Toxicol. Suppl.* 1980, 4, 428–430.] The cytotoxicity ($CD_{50}$) of a naturally-occurring humic acid for human peripheral blood leukocytes (PBL) was found to be 1–9 milligrams per milliliter. In addition, J. Schneider, R. Weis, C. Manner, B. Kary, A. Werner, B. J. Seubert, and U. N. Riede, *Virology* 1996, 218(2), 389–395, reported that the cytotoxicity of a synthetic humic acid prepared from hydroquinone for MT-2 cells was approximately 600 micrograms per milliliter. It has also been found that medicaments prepared from humic acids isolated from naturally-occurring soil materials are neither carcinogenic (Syrian hamster embryo cell transformation test: J. Koziorowska and E. Anuszewska, *Acta Pol. Pharm.* 1994, 51(1), 101–102) nor mutagenic (T. Sato, Y.

Ose, and H. Hagase, *Mutat. Res.* 1986, 162(2), 173–178; V. M. Sui, A. I. Kiung, and T. I. Veidebaum, *Vopr. Kurortol. Fiozioter. Lech. Fiz. Kult.* 1986, 2(3–4), 34–37; J. Koziorowska, B. Chlopkiewicz, and E. Anuszewska, *Acta Pol. Pharm.* 1993, 50(4–5), 379–382). Prenatal (S. Golbs, V. Fuchs, M. Kuhnert, and C. Polo, *Arch. Exp. Veterinarmed.* 1982, 36(2), 179–185) and embryotoxic and teratogenic effects (T. Juszkiewicz, M. Minta, B. Wlodarczyk, B. Biemacki, and J. Zmudzki, *Acta Pol. Pharm.* 1993, 50(4–5), 383–388) are also not observed with humic preparations at daily dose levels from 5–50 milligrams per kilogram body weight. Topical preparations are tolerated even better (V. V. Soldatov and M. N. Cherepanova, *Vopr. Kurortol. Fizioter. Lech. Fiz. Kult.* 1970, 35(3), 256–259; H. Czyzewska-Szafran, Z. Jastrzebski, D. Soltysiak-Pawluczuk, M. Wutkiewicz, A. Jedrych, and M. Remiszewska, *Acta Pol. Pharm.* 1993, 50(4–5), 373–377) when applied dermally in aqueous solution in amounts as high as 10 percent weight-by-volume (K. Wiegleb, N. Lange, and M. Kuhnert, *Dtsch. Tierarztl. Wochenschr.* 1993, 100(10), 412–416).

Because humic substances are not chemically well-defined, the preparation of synthetic humic acids whose physicochemical properties mimic naturally-occurring materials is quite difficult, as pointed out by K. Murray and P. W. Linder, *J. Soil Sci.* 1983, 34, 511–523. Nevertheless, there have been several notable advances in this area. Broadly speaking, three general strategies have evolved. All depend upon starting with well-defined molecules of molecular weight on the order of hydroxybenzoic acid, and then causing the molecules to polymerize upon themselves to form larger molecules. The methods differ in the causation factor, which can be microbial, chemical, or enzymatic.

Humic acids of microbial origin have been described and discussed by M. Robert-Gero, C. Hardisson, L. Le Borgne, and G. Pignaud, *Ann. Inst. Pasteur (Paris)* 1966, 111(6), 750–767; and by M. Robert-Gero, C. Hardisson, L. Le Borgne, and G. Vidal, *Ann. Inst. Pasteur (Paris)* 1967, 113(6), 903–909.

The chemical synthesis of humic acids has been pioneered by R. Klocking, B. Helbig, and associates: R. Klocking, B. Helbig, and P. Drabke, *Pharmazie* 1977, 32, 297; R. Klocking, B. Helbig, K. D. Thiel, T. Blumohr, P. Wutzler, M. Sprossig, and F. Schiller, *Pharmazie* 1979, 34(5–6), 293–294; R. Mentel, B. Helbig, R. Klocking, L. Dohner and M. Sprossig, *Biomed. Biochim. Acta* 1983, 42(10), 1353–1356; H. P. Klocking, R. Klocking, and B. Helbig, *Farmakol. Toksikol.* 1984, 47(1), 93–95; K. D. Thiel, P. Wutzler, B. Helbig, R. Klocking, M. Sprossig, and H. Schweizer, *Pharmazie* 1984, 39(11), 781–782; J. Hils, A. May, M. Sperber, R. Klocking, B. Helbig, and M. Sprossig, *Biomed. Biochim. Acta* 1986, 45(9), 1173–1179; B. Helbig, A. Sauerbrei, R. Klocking, P. Wutzler, N. Wicht, U. Wiedemann, and G. Herrmann, *J. Med. Virol.* 1987, 23(3), 303–309; K. I. Hanninen, R. Klocking, and B. Helbig, *Sci. Total Environ.* 1987, 62, 201–210; R. Klocking and B. Helbig, in *Humic Substances in the Aquatic and Terrestrial Environment;* New York: Springer-Verlag, 1989; 407–412; C. Schewe, R. Klocking, B. Helbig, and T. Schewe, *Biomed. Biochim. Acta* 1991, 50(3), 299–305; D. Schols, P. Wutzler, R. Klocking, B. Helbig, and E. De Clercq, *J. Acquir. Immune Defic. Syndr.* 1991, 4(7), 677–685. Typically, 10 millimoles of the starting small-molecule phenolic compound is dissolved in distilled water, the pH is adjusted to 8.5 with aqueous sodium hydroxide (NaOH), and then 2–5 millimoles of sodium periodate ($NaIO_4$) is added. The solution is warmed at 50° C. for 30 minutes, and is then allowed to stand overnight. The resultant humic acid-like polymeric products are isolated by precipitation with lead(II) nitrate [$Pb(NO_3)_2$]. The precipitated polymers are redissolved in aqueous sodium hydroxide (pH 8.5) and heated with 8-hydroxyquinoline for 30 minutes at 100° C. The precipitate formed is lead(II) chelate, which is removed by filtration. Residual 8-hydroxyquinoline is extracted with chloroform, and the desired polymeric material is then precipitated from the aqueous solution by the addition of various combinations of acetic acid, ethyl acetate, and ethanol. Starting compounds that have been used for the synthesis of humic-like materials include 4-[bis(p-hydroxyphenyl)methylene]-2,5-cyclohexadien-1-one (aurin), 4-[bis(3-carboxy-4-hydroxyphenyl)methylene]-2-carboxy-2,5-cyclohexadien-1-one (aurintricarboxylic acid), 3-(3,4-dihydroxyphenyl)propenoic acid (caffeic acid), 1,2-dihydroxybenzene (catechol), 1,3,4,5-tetrahydroxycyclohexanecarboxylic acid 3-(3,4-dihydroxyphenyl)propenoate (chlorogenic acid), 3,4-dihydroxyphenylacetic acid (homoprotocatechuic acid), 1-(3,4-dihydroxyphenyl)-2-(N-methylamino)ethanol (epinephrine), 3-(4-hydroxy-3-methoxyphenyl)-2-propenoic acid (ferulic acid), 3,4-5-trihydroxybenzoic acid (gallic acid), 2,5-dihydroxybenzoic acid (gentisic acid), 2,5-dihydroxyphenylacetic acid (homogentisic acid), 3-(3,4-dihydroxyphenyl)propionic acid (hydrocaffeic acid), 1,4-dihydroxybenzene (hydroquinone), 2,3-dihydroxytoluene (3-methylcatechol), 3,4-dihydroxytoluene (4-methylcatechol), 2,5-dihydroxytoluene (2-methylhydroquinone), 4,4'-(2,3-dimethyltetramethylene)-di-(1,2-dihydroxybenzene) (nordihydroguaiaretic acid), 1-(3,4-dihydroxyphenyl)-2-aminoethanol (norepinephrine), 3,4-dihydroxybenzoic acid (protocatechuic acid), 1,2,3-trihydroxybenzene (pyrogallol), 1,3-dihydroxybenzene (resorcinol), and 4-hydroxy-3-methoxybenzoic acid (vanillic acid). Other notable efforts on the chemical synthesis of humic-like substances include the studies by De Clercq and colleagues on aurintricarboxylic acid, its derivatives, and related compounds: M. Cushman, P. Wang, S. H. Chang, C. Wild, E. De Clercq, D. Schols, M. E. Goldman, and J. A. Bowen, *J. Med. Chem.* 1991, 34(1), 329–337; M. Cushman, S. Kanamathareddy, E. De Clercq, D. Schols, M. E. Goldman, and J. A. Bowen, *J. Med. Chem.* 1991, 34(1), 337–342. Related efforts have also been reported by M. Robert-Gero, C. Hardisson, L. Le Borgne, and G. Vidal, *Ann. Inst. Pasteur (Paris)* 1967, 113(6), 903–909; M. Jakubiec, E. Miszczak, and J. Szczerkowska, *Acta Microbiol. Pol.* [*B*] 1971, 3(1), 63–66; R. Ansorg and W. Rochus, *Arzneimittelforschung* 1978, 28(12), 2195–2198; J. Pommery, M. Imbenotte, A. F. Urien, D. Marzin, and F. Erb, *Mutat. Res.* 1989, 223(2), 183–189; F. J. Lu and Y. S. Lee, *Sci. Total Environ.* 1992, 114, 135–139; K. Wiegleb, N. Lange, and M. Kuhnert, *DTW Dtsch. Tierarztl. Wochenschr.* 1993, 100(10), 412–416; H. L. Yang, F. J. Lu, S. L. Wung, and H. C. Chiu, *Thromb. Haemost.* 1994, 71(3), 325–330; W. Seffner, F. Schiller, R. Heinze, and R. Breng, *Exp. Toxicol. Pathol.* 1995, 47(1), 63–70; and J. Schneider, R. Weis, C. Manner, B. Kary, A. Werner, B. J. Seubert, and U. N. Riede, *Virology* 1996, 218(2), 389–395.

The enzymatic catalytic synthesis of humic acids dates to about 1961 with the work by R. E. Hampton and R. W. Fulton, *Virology* 1961, 13, 44–52 (see also R. E. Hampton, *Phytophathology* 1970, 60, 1677–1681), who found that enzymatically oxidized phenols inactivate phytopathogenic (i.e., plant-related) viruses. Typically o-diphenol oxidase has been employed for the enzymatic synthesis of humic-like materials: anon. *Zentralbl Bakteriol.* [*Orig. A*] 1976, 234(2), 159–169; R. Klocking, B. Helbig, and P. Drabke, *Pharmazie* 1977, 32(5), 297; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782; and G. Sydow, V. Wunderlich, R. Klocking, and B. Helbig, *Pharmazie* 1986, 41(12), 865–868.

A direct comparison of humic acids synthesized enzymatically and nonenzymatically from caffeic and hydrocaffeic acids has shown that the two synthetic routes produce materials that differ somewhat in their efficacy for the suppression of herpes (hominis) types 1 and 2 viruses: K. D. Thiel, P. Wutzler, B. Helbig, R. Klocking, M. Sprossig, and H. Schweizer, *Pharmazie* 1984, 39(11), 781–782.

PCT application WO 00/16785 (Mar. 30, 2000) from Dekker and Medlen discloses the use of humic acid or its salts, esters, or derivatives thereof, all prepared as described in U.S. Pat. Nos. 4,912,256 and 5,004,831 from coal extracts, in stimulating lymphocytes in a human, animal, or bird. This allows for the treatment of viral and bacterial infections, and more particularly HIV infections, cancer, and opportunistic diseases. Oxihumic acids, salts, esters, or derivatives thereof are preferred. Administration is preferably oral. Some example pharmacological data presented include the antiviral activity of oxihumates against HIV-1 in vitro and clinical trials of oral oxihumate in HIV-infected patients.

PCT application WO 00/16786 (Mar. 30, 2000) from Dekker and Medlen discloses the use of pharmaceutical compositions comprising an oxihumic acid or its salts, esters, or derivatives thereof, all prepared as described in U.S. Pat. Nos. 4,912,256 and 5,004,831 from coal extracts, as active ingredients. Compositions are preferably administered orally for stimulating lymphocytes in a human, animal, or bird. They may be used in treating viral and bacterial infections, HIV infections, opportunistic diseases, inflammation, pain and fever, cancer growth, and diseases associated with viral infection and a depressed immune system. A number of pharmacological examples are given, including interleukin 10 production by oxihumate-treated lymphocytes, increased antibody production against Newcastle disease in chickens treated with oxihumate, TNF production by oxihumate-treated lymphocytes, and antiviral activity of oxihumate against HSV-1 and coxsackie virus type 1 in vitro.

The diversity of physicochemical characteristics as well as wide variation in the biological activity and toxicity of humics extracted or otherwise derived from natural soils has been well documented. This diversity and variation is due to variations in factors such as the source of the soil, the method(s) of extraction and/or isolation, and the technique(s) employed to treat the extract once it has been separated and isolated from crude soil. The consequence of irreproducibility of the properties of substances extracted from natural soil is that the commercial value of such materials is minimized. In addition, they are rendered unsuitable as medicaments. Also, while a number of laboratory-scale processes have already been described that address various aspects of the isolation, synthesis, and/or preparation of humic substances or similar materials, there are no reports of preparing and isolating such purely synthetic humic acids or similar materials by methods that are suitable for scaleup directly to industrial levels, that provide economically acceptable yields, and that optimize the preparation procedures from the standpoint of medicament safety and efficacy.

Also, all of the known synthetic methods utilize potentially toxic precipitation methods, such as lead(II) nitrate precipitation; followed by complex isolation procedures, such as potentially mutagenic compound-producing hydrochloric acid precipitation; or lengthy synthetic steps as long as 10 days.

SUMMARY OF THE INVENTION

There is a need to devise simple synthetic procedures that yield inexpensive, safe materials whose physicochemical attributes are reproducible, and that at least simulate those of typical commercially-available soil extracts. There is a need for a safe, efficacious and simple method for treating blood products, especially human blood products, to reduce or eliminate lipid enveloped and non-enveloped virus activity without loss of blood product or blood product activity.

One embodiment is a method for preventing and/or treating hemorrhagic fever virus infection in a mammal which comprises administering an effective amount of a synthetic phenolic polymeric material which is prepared by:

A) Dissolving the starting organic compound or mixture of organic compounds in an aqueous solution;

B) Oxidizing and polymerizing the organic compound or mixture of organic compounds;

C) Adding one or more compounds or salts selected from the group consisting of boric acid, borate salts, alkaline earth salts, transition metal salts, alkaline sulfides, alkaline earth sulfides or transition metal sulfides to the aqueous solution resulting from step B);

D) Allowing the aqueous solution resulting from step C) to stand with or without stirring at between about 20° C. and 100° C. for a period of at least about 2 hours; and E) Removing molecules from the solution resulting from step F) below about 500 daltons to 10,000 daltons.

In another aspect, the step of oxidizing and polymerizing the starting organic compound can be achieved by adjusting the pH of the aqueous solution to between about 8 and 11, adding an alkaline periodate or alkaline-earth periodate salt to the aqueous solution, and maintaining the temperature of the solution between about 20° C. and 100° C. for a period of at least about 30 minutes.

In another aspect, the method of preparation of the synthetic phenolic polymeric material further comprises a step, following the step of removing molecules from the solution below about 500 daltons to 10,000 daltons, of concentrating the solution.

In another aspect, the method of preparation of the synthetic phenolic polymeric material further comprises a step, following the step of removing molecules from the solution below about 500 dalton to 10,000 daltons, of removing water from the solution.

In another aspect, the hemorrhagic fever virus infection is effected by a virus of arenavirus or bunyavirus, preferably Pichinde hemorrhagic fever virus or Punta Toro A hemorrhagic fever virus.

In another aspect, the administering of a synthetic phenolic polymeric material is along with an effective amount of an antiviral composition.

In another aspect, the administering of a synthetic phenolic polymeric material can be achieved systemically or topically.

One embodiment is a method for inhibiting hemorrhagic fever viral attachment to host cells in a mammal which comprises administering an effective amount of a synthetic phenolic polymeric material which is prepared by:

A) Dissolving the starting organic compound or mixture of organic compounds in an aqueous solution;

B) Oxidizing and polymerizing the organic compound or mixture of organic compounds;

C) Adding one or more compounds or salts selected from the group consisting of boric acid, borate salts, alkaline earth salts, transition metal salts, alkaline sulfides, alkaline earth sulfides or transition metal sulfides to the aqueous solution resulting from step B);

D) Allowing the aqueous solution resulting from step C) to stand with or without stirring at between about 20° C. and 100° C. for a period of at least about 2 hours; and E) Removing molecules from the solution resulting from step F) below about 500 daltons to 10,000 daltons.

In another aspect, the step of oxidizing and polymerizing the starting organic compound can be achieved by adjusting the pH of the aqueous solution to between about 8 and 11, adding an alkaline periodate or alkaline-earth periodate salt to the aqueous solution, and maintaining the temperature of the solution between about 20° C. and 100° C. for a period of at least about 30 minutes.

In another aspect, the method of preparation of the synthetic phenolic polymeric material further comprises a step, following the step of removing molecules from the solution below about 500 daltons to 10,000 daltons, of concentrating the solution.

In another aspect, the method of preparation of the synthetic phenolic polymeric material further comprises a step, following the step of removing molecules from the solution below about 500 dalton to 10,000 daltons, of removing water from the solution.

DETAILED DESCRIPTION OF THE PREFERRED EMBODIMENT

Figure 1:
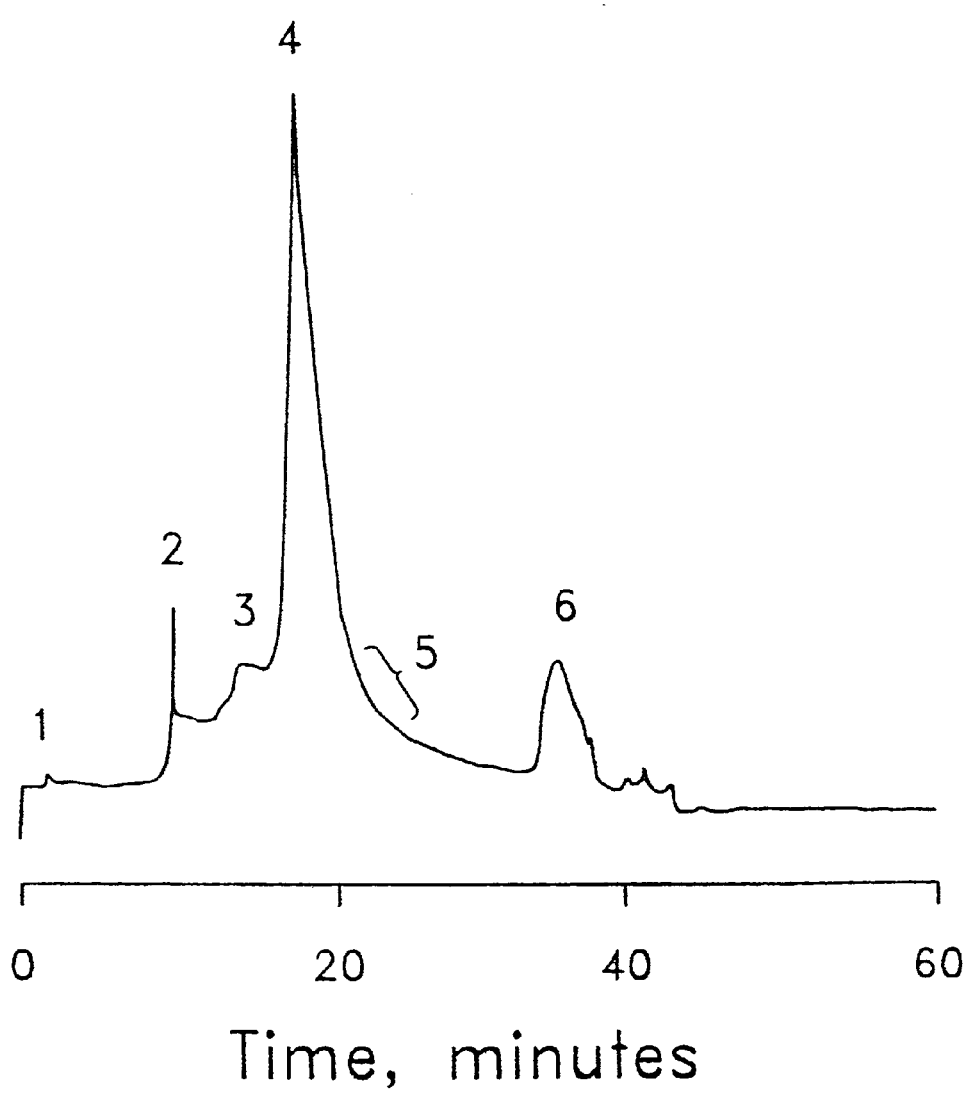
FIG. 1 shows a high-performance liquid chromatography (HPLC) trace for the synthetic humic acid product obtained from 2,5-dihydroxyphenylacetic acid (homogentisic acid), as described in Examples 10, 11, and 12.

U.S. Pat. No. 5,945,446, issued Aug. 31, 1999, discloses the process for preparing synthetic soil-extract materials and medicaments based thereon. U.S. Pat. No. 5,945,446 and the references therein are incorporated herein by reference in their entirety.

The inventor has developed combinations of chemical processes for the preparation of synthetic phenolic polymeric materials, also known as synthetic humic acids, whose physicochemical properties and attributes are reproducible, and which simulate those of typical commercially-available natural humic acids and other soil extracts, which contain little or no ionic salts or other compounds of molecular weight less than 500 daltons, which have a minimum molecular weight of 500 daltons, and which processes shall be suitable for scaleup directly to industrial levels that provide economically acceptable yields.

The inventor has also developed compositions and methods for treating or preventing hemorrhagic fever viral diseases by using an effective amount for anti-viral activity of a synthetic humic acid prepared according to the above processes.

Hemorrhagic fever viral diseases are caused by any of the four distinct families of viruses: arenaviridae, filoviridae, bunyaviridae, and flaviviridae. Genera of arenaviridae include arenavirus. A selection of species of arenaviridae includes lymphocytic choriomeningitis virus, Lassa virus, Junin virus, Machupo virus, Guanarito virus, Sabia virus, and Pichinde virus. Genera of filoviridae include Ebola virus and Marburg virus. Genera of bunyaviridae include bunyavirus, hantavirus, nairovirus, phelobovirus, and Tospovirus. A selection of species of bunyaviridae includes Punta Toro virus, Rift Valley fever virus, Crimean-Congo hemorrhagic fever virus, and Hataan virus. Genera of flaviviridae include flavivirus, pestivirus, and hepatitis-C-like virus. Examples of species of flaviviridae include yellow fever virus, dengue virus, Omsk hemorrhagic fever virus, and Kyansanur forest disease virus.

The starting compounds used in the chemical processes employed for production of synthetic humic acids according to particularly preferred embodiments are known materials that are readily available commercially.

A preferred embodiment of the chemical processes for the preparation of synthetic humic acids includes the following steps:

A) Dissolving the starting organic compound or mixture of organic compounds in an aqueous solution;

B) Adjusting the pH of the aqueous solution resulting from step A) to betwen about 8 and 11 if necessary;

C) Adding an alkaline periodate salt or alkaline-earth periodate salt, to the aqueous solution resulting from step B);

D) Maintaining the temperature of the solution resulting from step C) between about 20° C. and 100° C. for a period of at least about 30 minutes;

E) Adding one or more compounds or salts selected from the group consisting of boric acid, borate salts, alkaline earth salts, transition metal salts, alkaline sulfides, alkaline earth sulfides or transition metal sulfides to the aqueous solution resulting from step D);

F) Allowing the aqueous solution resulting from step E) to stand with or without stirring at a temperature between about 20° C. and 100° C. for a period of at least about 2 hours;

G) Removing molecules from the solution resulting from step F) below about 500 daltons to 10,000 daltons;

H) Concentrating the solution resulting from step G); and

I) Removing the water from the solution resulting from step H), if necessary.

The starting organic compound in step A) above can be one, or more than one in combination, of different organic compounds comprising at least one hydroxyl group and at least one carbonyl group or at least two hydroxyl groups on an aromatic structure. The Examples herein include both types of starting organic compounds. Examples of compounds comprising at one hydroxyl group and at least one carbonyl group include aurintricarboxylic acid and tetrahydroxybenzoquinone. Examples of starting organic compounds comprising at least two hydroxyl groups on an aromatic structure include hydroquinone and norepinephrine.

Particularly preferred starting organic compounds are illustrated in Tables 1 and 2. Starting organic compounds illustrated in Table 1 are comprised of a single benzene ring with six substituents $R_1$–$R_6$, wherein $R_1$–$R_6$ can be any one of the indicated atom or functional groups, as long as at least one of $R_1$–$R_6$ is a hydroxy (—OH) functional group. Preferably, at least one of $R_1$–$R_6$ is a hydroxy (—OH) functional group and at least one of the remaining substituents $R_1$–$R_6$ contains a carboxylic acid functional group.

More preferably, two of $R_1$–$R_6$ are hydroxy (—OH) functional groups and one of the remaining substituents $R_1$–$R_6$ contains a carboxylic acid functional group. Homogentisic acid, which is 2,5-dihydroxyphenylacetic acid, is a particularly preferred starting organic compound. Caffeic acid, which is 3,4-dihydroxycinnamic acid, is another particularly preferred starting organic compound. Chlorogenic acid, which is 1,3,4,5-tetrahydroxycyclohexanecarboxylic acid 3-(3,4-dihydroxycinnamate) is yet another particularly preferred starting organic compound.

TABLE 1

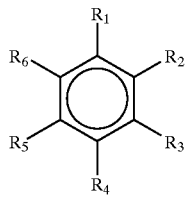

$R_1$, $R_2$, $R_3$, $R_4$, $R_5$, $R_6$ =
—H
—$CH_3$
—$CH_2CH_3$
—$(CH_2)_2CH_3$
—$CH(CH_3)_2$
—OH
—$OCH_3$
—CHO
—$CO_2H$
—$CO_2CH_3$
—$CH_2OH$
—$CH_2OCH_3$
—$CH_2CHO$
—$CH_2CO_2H$
—$CH_2CO_2CH_3$
—$(CH_2)_2OH$
—$(CH_2)_2OCH_3$
—$(CH_2)_2CHO$
—$(CH_2)_2CO_2H$
—$(CH_2)_2CO_2CH_3$
—$CH(CH_3)OH$
—$CH(CH_3)OCH_3$
—$CH(CH_3)CHO$
—$CH(CH_3)CO_2H$
—$CH(CH_3)CO_2CH_3$
—$CH(CH_3)CH_2OH$
—$CH(CH_3)CH_2OCH_3$
—$CH(CH_3)CH_2CHO$
—$CH(CH_3)CH_2CO_2H$
—$CH(CH_3)CH_2CO_2CH_3$
—$CH(OH)_2$
—$CH(OH)OCH_3$
—$CH(OH)CHO$
—$CH(OH)CO_2H$
—$CH(OH)CO_2CH_3$
—$CH(OCH_3)OH$
—$CH(OCH_3)_2$
—$CH(OCH_3)CHO$
—$CH(OCH_3)CO_2H$
—$CH(OCH_3)CO_2CH_3$
—$CH(OH)CH_2OH$
—$CH(OH)CH_2OCH_3$
—$CH(OH)CH_2CHO$
—$CH(OH)CH_2CO_2H$
—$CH(OH)CH_2CO_2CH_3$
—$CH(OCH_3)CH_2OH$
—$CH(OCH_3)CH_2OCH_3$
—$CH(OCH_3)CH_2CHO$
—$CH(OCH_3)CH_2CO_2H$
—$CH(OCH_3)CH_2CO_2CH_3$
—$(CH_2)_3OH$
—$(CH_2)_3OCH_3$
—$(CH_2)_3CHO$
—$(CH_2)_3CO_2H$
—$(CH_2)_3CO_2CH_3$

TABLE 1-continued

—CHCHOH (cis or trans)
—$CHCHOCH_3$ (cis or trans)
—CHCHCHO (cis or trans)
—$CHCHCO_2H$ (cis or trans)
—$CHCHCO_2CH_3$ (cis or trans)
—$CH_2CHCHOH$ (cis or trans)
—$CH_2CHCHOCH_3$ (cis or trans)
—$CH_2CHCHCHO$ (cis or trans)
—$CH_2CHCHCO_2H$ (cis or trans)
—$CH_2CHCHCO_2CH_3$ (cis or trans)

TABLE 2

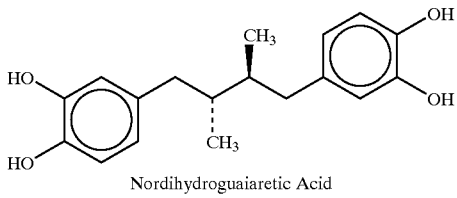
Nordihydroguaiaretic Acid

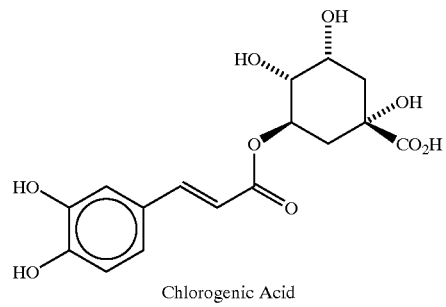
Chlorogenic Acid

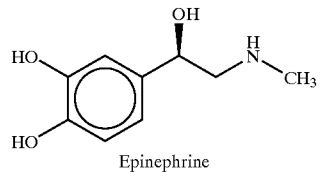
Epinephrine

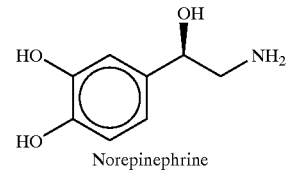
Norepinephrine

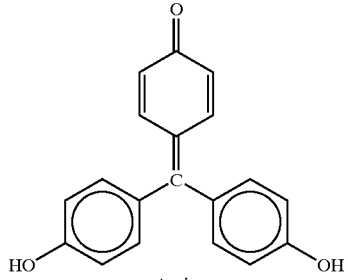
Aurin

TABLE 2-continued

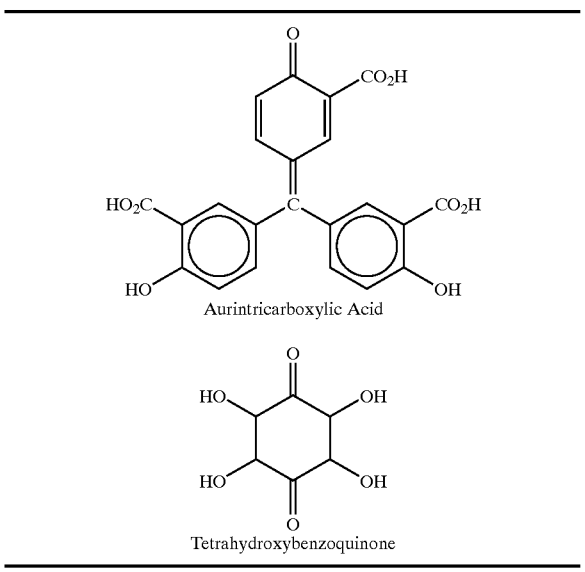

Aurintricarboxylic Acid

Tetrahydroxybenzoquinone

Various initial concentrations of starting organic compounds in water can be employed and no lower or upper limits are uniformly required. A low concentration solution of sodium hydroxide, such as 0.1 Normal, may also be employed as a diluent for the starting organic compound. The appropriate initial concentration of the starting organic compound or compounds is determined by the synthesis yield requirements and inherent requirements, such as the upper limit of aqueous solubility of the starting organic compound or compounds. Conventional methods are employed to determine the appropriate initial concentration of the starting organic compound or compounds.

The pH of the aqueous solution containing the starting organic compound or compounds can be adjusted in step B) to between about 8 and 11 by adding aqueous ammonium hydroxide, or other aqueous alkaline oxide or hydroxide, or aqueous alkaline earth oxide or hydroxide, or aqueous transition metal oxide or hydroxide. Additionally, if the initial aqueous solution contains a low concentration of base, such as 0.1 Normal sodium hydroxide and the initial solution pH is too high, an acid such as hydrochloric acid may be employed to adjust the pH to the desired value. Other inorganic acids may also be employed for pH adjustment. Note that if hydrochloric acid is employed to adjust the pH downward from an initial high value, care should be taken to avoid letting the pH go below 8. Acidic conditions below pH 7 should be avoided in the presence of hydrochloric acid to eliminate the possibility of formation of mutagenic chlorinated humic acid materials.

An alkaline periodate salt or alkaline earth periodate salt may be employed as an oxidant or polymerization initiator of the starting organic compound in step C). Sodium periodate is particularly preferred. The concentration of the alkaline periodate salt or alkaline earth periodate salt is generally between about 10% and 100% of the starting organic compound or compounds on a molar basis. Thus, if 10 millimoles of starting organic compound is employed, 1 to 10 millimoles of alkaline periodate salt may be employed. Preferably, a molar concentration of periodate that is about 10%–50% of the molar concentration of the starting organic compound or compounds is employed. Most preferably, a molar concentration of periodate that is about 25%–35% of the molar concentration of the starting organic compound or compounds is employed. The exact concentration to be used can be determined by conventional synthetic yield optimization techniques.

Alkaline or alkaline earth sulfides or transition metal sulfides can be optionally added to the initial aqueous solution containing the starting organic compound or compounds following the pH adjustment in step B) and immediately before, at the same time, or following the addition of the periodate in step C). Sulfides contribute to the phenolic polymeric structure, the stability of the structure and its biological activity. Sodium sulfide nonahydrate is a particularly preferred sulfide. The concentration of the sulfide is generally between about 1% and 20% of the starting organic compound or compounds on a molar basis. Thus, if 10 millimoles of starting organic compound is employed, 0.1 to 2 millimoles of sulfide may be employed. Preferably, a molar concentration of sulfide that is about 5%–15% of the molar concentration of the starting organic compound or compounds is employed. Most preferably, a molar concentration of sulfide that is about 8% to 12% of the molar concentration of the starting organic compound or compounds is employed. The exact concentration of sulfide to be used can be determined by conventional synthetic yield optimization techniques.

The pH-adjusted aqueous solution containing the starting organic compound, periodate and optional sulfide is placed in a water-bath or other thermostat heating device at about 20° C. to 100° C. for a period of about 30 minutes to 100 hours in step D). Alternatively, the aqueous solution itself may be thermostated between about 20° C. and 100° C. for a period of about 30 minutes to 100 hours. A preferred temperature and time period is between about 35° C. and 80° C. for about 30 minutes to 100 hours. A particularly preferred temperature and time is about 50° C. for about 30 minutes to two hours. Alternative temperatures and pressures that are equivalent to the above temperature and pressures may be used.

Steps B) and C) above give conditions for oxidizing and polymerizing the starting organic compound. Although the use of periodate salt in basic conditions is preferable, there are other conditions that can perform oxidation and polymerization of the starting organic compound. One may substitute other reagents known in the art that are known to perform this function. If the reagents for oxidation and polymerization are substituted, the temperature and time period for the reaction in step D) should be adjusted accordingly for optimization. For example, a phenolic solution with 2 equivalents of hydrogen peroxide can react for one week at 23° C. to form humic acids.

Following this period, salts are added to the solution resulting from step D) alone or in combination in step E). Salts containing boron, calcium and other alkaline earths, iron and other transition metals are preferred. Such salts may contribute to the phenolic polymeric structure, its stability and biological activity. Boric acid or boron-containing-borate salts, such as sodium borate, are particularly preferred, as are alkaline earth salts, such as calcium sulfate dihydrate, and transition metal salts, such as ferrous sulfate heptahydrate. The concentrations of each of the salts employed is generally between about 0.1% and 20% of the starting organic compound or compounds on a molar basis. Preferably, a molar concentration of salt which is about 0.2% to 10% of the molar concentration of the starting organic compound or compounds is employed. Most preferably, a molar concentration of salt that is about 0.2% to 2% of the molar concentration of the starting organic compound or compounds, is employed. The exact concentration to be used can be determined by conventional synthetic yield optimization techniques. The solution resulting from step E) is allowed to stand at between about 20° C. and 100° C. with or without stirring for a period of at least 2 hours in step F). Preferably, the solution is allowed to stand at between about 20° C. and 80° C. for about 2 to 48 hours. Alternative temperatures and pressures that are equivalent to the above temperature and pressures may be used. Any precipitate formed at this stage is removed via conventional centrifugation.

Molecules below about 500 to about 10,000 daltons in the solution resulting from step F) are removed in step G). A variety of known conventional techniques can be employed, such as preparative chromatography, ultrafiltration or dialysis. Molecules are preferably removed from the solution resulting from step F) by employing dialysis in step G) with a flow-through open-channel or screen membrane apparatus consisting of a sandwich-type membrane of lower molecular-weight cutoff of 500–10,000 daltons until the conductivity of the solution has dropped to about 200 microsiemens or less. Most preferably, molecules are removed from the solution resulting from step F) by employing dialysis in step G) until the conductivity of the solution has dropped to about 50 microsiemens or less. A Pall Filtron Ultrasette® Tangential Flow Device or Mini-Ultrasette® Tangential Flow Device used with a Pall Filtron Ultralab® Specialized Pump and Reservoir System is preferred for solution dialysis.

The conductivity of the solution processed in step G) above can conveniently be monitored with a flow-through conductivity cell and conductivity meter. Alternatively, a simple inexpensive hand-held combination conductivity cell/conductivity meter (e.g., a Nalcometer Model MLN) can be employed.

Before removing the water from the above solution in step H), the solution resulting from step G) above can be further dialyzed with a flow-through apparatus consisting of a sandwich-type membrane of molecular weight cutoff of 50,000 daltons. In this case, the filtrate solution, not the retentate, is saved for further concentrating and processing according to steps H) and I). The resultant product will have a molecular-weight range of 500–50,000 daltons.

If the solution resulting from either steps G) or H) above is to be stored as an aqueous solution for long periods of time for later application or use, for example as an anti-viral treatment solution, anti-viral therapy, anti-microbial therapy, a spray-on fertilizer or soil amendment, it can be filtered through standard 0.2–0.4 micron filters to remove bacteria and viruses, that is, can be made sterile by filtration. Alternatively, the aqueous solution from either steps G) or H) can be autoclaved for about 5–60 minutes at about 100–150° C. to produce a sterile solution.

A final optional step I) in the process involves removing water from the solution resulting from step H). When freeze-drying is employed as the method of water removal in step I) above, the resultant product is a light fluffy dark-colored powder that is subject to static electricity effects. To minimize these effects, a small amount of mannose or other sugar can be added to the solution resulting from step H) just prior to freeze-drying. Water removal from the product can be carried out by means other than freeze-drying in step I) above, such as by heat evaporation with or without vacuum, by rotary evaporation, by spray-drying, or by any other solvent-removal technique that is convenient as well as economical for aqueous solutions. The dried powder obtained from step I) above can be autoclaved for about 15–30 minutes at about 100–120° C. to produce a sterile powder.

The synthetic humic acid materials produced according to the chemical processes and separation and isolation procedures of the preferred embodiments exhibit the physicochemical properties and attributes of typical naturally-occurring commercially-available humic acids and other soil extracts.

A facile method of examining the physicochemical characteristics of the product yielded by steps A) through H) above, or by modifications thereto, is high performance liquid chromatography (HPLC). The chromatographic fingerprint pattern so obtained from HPLC also offers a convenient means of comparing one product with another, as well as comparing each of the synthetic products with naturally-occurring humic acids and other soil-extract materials. The HPLC method is thus used to determine the reproducibility of the physiochemical properties and attributes of the synthetic phenolic polymeric materials, as well as to determine if the aforementioned properties and attributes simulate the physiochemical properties and attributes of typical commercial-available natural humic acids and other soil extracts. The latter determination of simulation is done in the conventional manner employing HPLC; e.g., by visually and quantitatively comparing the HPLC chromatographic fingerprint patterns of the materials. The fingerprint patterns of the two materials, one synthetic and one natural, need not be 100% identical to conclude that the physiochemical properties and attributes of the synthetic phenolic polymeric material simulates the physiochemical properties and attributes of the natural humic acid. An approximate correspondence between the aforementioned HPLC fingerprint patterns is all that is required to conclude that the synthetic material simulates the natural material. In general, even a 75% visual correspondence in two HPLC fingerprint patterns is all that is necessary to conclude that one material simulates another.

A useful fingerprint pattern for natural as well as synthetic soil extract materials can be obtained as follows. The column comprises packing, typically reversed-phase polymer PRP-1 (Hamilton Co.), of particle size 5 microns, and being 150 millimeters in length by 4.1 millimeters inside diameter. The mobile phase comprises three solutions: Solution A, Solution B, and Solution C. Solution A is 0.1 Normal aqueous sodium hydroxide. Solution B is 0.05 Normal of so-called Prideaux universal buffer, which is made by combining 4.25 grams of sodium nitrate ($NaNO_3$), 12.37 grams of boric acid ($H_3BO_3$), 23.06 grams of phosphoric acid ($H_3PO_4$), and 12.01 grams of acetic acid ($CH_3CO_2H$) with 4 liters of distilled water. Solution C is 100% methanol ($CH_3OH$). The mobile-phase gradient employed for an HPLC run consists of 40% solution A plus 60% solution B at the beginning, which composition is changed in a linear manner to 100% solution A after 20 minutes. The mobile phase is then changed linearly again to 10% A plus 90% C over the next 5 minutes, which final composition is held for the purpose of a column wash for the next 35 minutes. The mobile-phase flow rate is 1 milliliter per minute. The detector is UV-Visible, which is set at 340 nanometers. The chart speed is typically 0.5 centimeter per minute. The sample loop size is 5–20 microliters. Solutions are prepared for HPLC by dissolving 0.1–10 grams of dried sample in 100 milliliters of distilled water or 0.1 Normal aqueous sodium hydroxide of pH 8–10.

The chemical processes and separation and isolation procedures of the preferred embodiments are suitable for scale-up directly to industrial levels that provide economically acceptable yields. The chemical processes and separation and isolation procedures of the preferred embodiments can produce synthetic product yields approaching 100%. More typically, about 0.8 to 0.65 g of synthetic humic acid can be produced from about 10 millimoles of starting organic compound or compounds in 300 milliliters. These procedures can be scaled up to pharmaceutical production scales employing about 10,000 to 20,000 liters or more of initial solution containing the starting organic compound or compounds. A total yield between about 2.7 and 21.7 kilograms of synthetic humic acid can be achieved utilizing a 10,000-liter thermally-jacketed stainless-steel tank and a concentration of starting organic compound of about 10 millimoles per 300 milliliters. A single anti-viral treatment may employ milligram amounts of synthetic humic acid. Twenty kilograms of synthetic humic acid represents 2 million units of anti-viral product at 10 milligrams per unit. Even at a treatment cost of $0.10 per unit, this amount represents $200,000.00 of synthetic humic acid. Since the starting organic compounds utilized in the preferred embodiments are relatively inexpensive, the synthesis yields of the chemical processes and separation and isolation procedures are economically very acceptable.

Examples 1 through 9 are illustrative of the variety of starting organic compounds that can be employed in the process of the preferred embodiments. It was not considered necessary to carry out all steps of the process to illustrate starting compound variety. More particularly, Examples 1 through 9 are illustrative of all steps of the process with the exception of step E), the addition of salts.

EXAMPLE 1

Preparation of a Synthetic Humic Acid from 2,5-Dihydroxybenzoic Acid (Gentistic Acid)

The starting organic compound is 2,5-dihydroxybenzoic acid (gentisic acid), shown in Table 1, represented by $R_1$=—$CO_2H$, $R_2,R_5$=—OH, and $R_3,R_4,R_6$=—H. Gentisic acid (1.55 grams, 10 mmoles) was dissolved in 300 milliliters of 0.1 N aqueous sodium hydroxide (NaOH). The solution pH was adjusted to 8.5 with 6 N HCl. Sodium periodate (0.54 gram, 2.5 mmoles) was added, and the solution was placed in a water-bath at 50° C. for 30 minutes. The solution was allowed to stand at room temperature overnight. Any precipitate was removed by centrifugation. The solution was dialyzed with a 1,000-dalton cut-off flow-through open-channel or screen membrane system (Pall Filtron: Ultrasette® 7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Five to twenty hundredths of a gram of mannose or other suitable carbohydrate can be added to the solution prior to freeze-drying to reduce static electricity effects associated with the freeze-dried powder.) The yield of synthetic soil extract was 0.2 gram.

The following Examples 2–9 employ the synthesis procedure of Example 1 beginning with the adjustment of solution pH.

EXAMPLE 2

Preparation of a Synthetic Humic Acid from 3,4-Dihydroxyphenylacetic Acid (Homoprotocatechuic Acid)

The starting organic compound is 3,4-dihydroxyphenylacetic acid (homoprotocatechuic acid), shown in Table 1, represented by $R_1$=—$CH_2CO_2H$, $R_3,R_4$=—OH, and $R_2,R_5,R_6$=—H. Homoprotocatechuic acid (1.68 grams, 10 mmoles) was dissolved in 300 milliliters of 0.1 N aqueous sodium hydroxide (NaOH). The remaining procedure followed that of Example 1. The yield of synthetic soil extract was 0.24 gram.

EXAMPLE 3

Preparation of a Synthetic Humic Acid from dl-(3, 4-Dihydroxyphenyl)hydroxyacetic Acid (dl-3,4-Dihydroxymandelic Acid)

The starting organic compound is dl-(3,4-dihydroxyphenyl)hydroxyacetic acid (dl-3,4-dihydroxymandelic acid), shown in Table 1, represented by $R_1$=—$CH(OH)CO_2H$, $R_3,R_4$=—OH, and $R_2,R_5,R_6$=—H. dl-3,4-Dihydroxymandelic acid (1.68 grams, 10 mmoles) was dissolved in 300 milliliters of 0.1 N aqueous sodium hydroxide (NaOH). The remaining procedure followed that of Example 1. The yield of synthetic soil extract was 0.08 gram.

EXAMPLE 4

Preparation of a Synthetic Humic Acid from Aurintricarboxylic Acid

The starting organic compound is aurintricarboxylic acid, shown in Table 2. Aurintricarboxylic acid (4.2 grams, 10 mmoles) was dissolved in 300 milliliters of 0.1 N aqueous sodium hydroxide (NaOH). The remaining procedure followed that of Example 1. The yield of synthetic soil extract was 4.7 grams.

EXAMPLE 5

Preparation of a Synthetic Humic Acid from 3-(3,4-Dihydroxyphenyl)Propenoic Acid (Caffeic Acid)

The starting organic compound is 3-(3,4-dihydroxyphenyl)propenoic acid (caffeic acid), shown in Table 1, represented by $R_1$=—$CHCHCO_2H$, $R_3,R_4$=—OH, and $R_2,R_5,R_6$=—H. Caffeic acid (1.80 grams, 10 mmoles) was dissolved in 300 milliliters of 0.1 N aqueous sodium hydroxide (NaOH). The remaining procedure followed that of Example 1. The yield of synthetic soil extract was 0.65 gram.

EXAMPLE 6

Preparation of a Synthetic Humic Acid from Tetrahydroxybenzoquinone

The starting organic compound is tetrahydroxybenzoquinone, shown in Table 2. Tetrahydroxybenzoquinone (1.72 grams, 10 mmoles) was dissolved in 300 milliliters of 0.1 N aqueous sodium hydroxide (NaOH). The remaining procedure followed that of Example 1. The yield of synthetic soil extract was 0.016 gram.

EXAMPLE 7

Preparation of a Synthetic Humic Acid from 1,4-Dihydroxybenzene (Hydroquinone)

The starting organic compound is 1,4-dihydroxybenzene (hydroquinone), shown in Table 1, represented by $R_1,R_4$=—OH, and $R_2,R_3,R_6$=—H. Hydroquinone (1.10 grams, 10 mmoles) was dissolved in 300 milliliters of 0.1 N aqueous sodium hydroxide (NaOH). The remaining procedure followed that of Example 1. The yield of synthetic soil extract was 0.16 gram.

EXAMPLE 8

Preparation of a Synthetic Humic Acid from 3,4,5-Trihydroxybenzoic Acid (Gallic Acid)

The starting organic compound is 3,4,5-trihydroxybenzoic acid (gallic acid), shown in Table 1, represented by $R_1$=—$CH_2CO_2H$, $R_3,R_4,R_5$=—OH. Gallic acid (1.70 grams, 10 mmoles) was dissolved in 300 milliliters of 0.1 N aqueous sodium hydroxide (NaOH). The remaining procedure followed that of Example 1. The yield of synthetic soil extract was 0.10 gram.

EXAMPLE 9

Preparation of a Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid was (1.68 grams, 10 mmoles) dissolved in 300 milliliters of 0.1 N aqueous sodium hydroxide (NaOH). The remaining procedure followed that of Example 1. The yield of synthetic soil extract was 0.20 gram.

The following Examples 10–14 are illustrative of a process of the preferred embodiments including step E), addition of salts. Addition of salts increases the activity of the synthetic humic acids produced by the method. Examples 10–14 illustrate that the synthetic humic acid materials produced according to the chemical processes and separation and isolation procedures of the preferred embodiments exhibit the physicochemical properties and attributes of typical naturally-occurring commercially-available humic acids and other soil extracts. Examples 10–14 also illustrate that the therapeutic indications of the synthetic humic acids produced according to the chemical processes and separation and isolation procedures of the preferred embodiments are those of soil extracts and humic acids in general, that is to say for viral-related disorders and diseases.

EXAMPLE 10

Preparation of Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_1$=—OH, and $R_3,R_4,R_6$=—H. Homogentisic acid (1 gram, 6 mmoles) was dissolved in 300 milliliters of 0.1 N aqueous sodium hydroxide (NaOH). The solution pH was adjusted to 8.5 with 6 N HCl. Sodium periodate (0.32 gram, 1.5 mmoles) and sodium sulfide nonahydrate (0.12 gram, 0.5 millimole) was added, and the solution was placed in a water, bath at 50° C. overnight. Boric acid (0.001 gram, 0.016 millimole), ferrous sulfate heptahydrate (0.021 gram, 0.075 millimole), and calcium sulfate dihydrate (0.006 gram, 0.035 millimole) were added and the solution was stirred for 2 hours at room temperature. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.23 gram.

Figure 2:
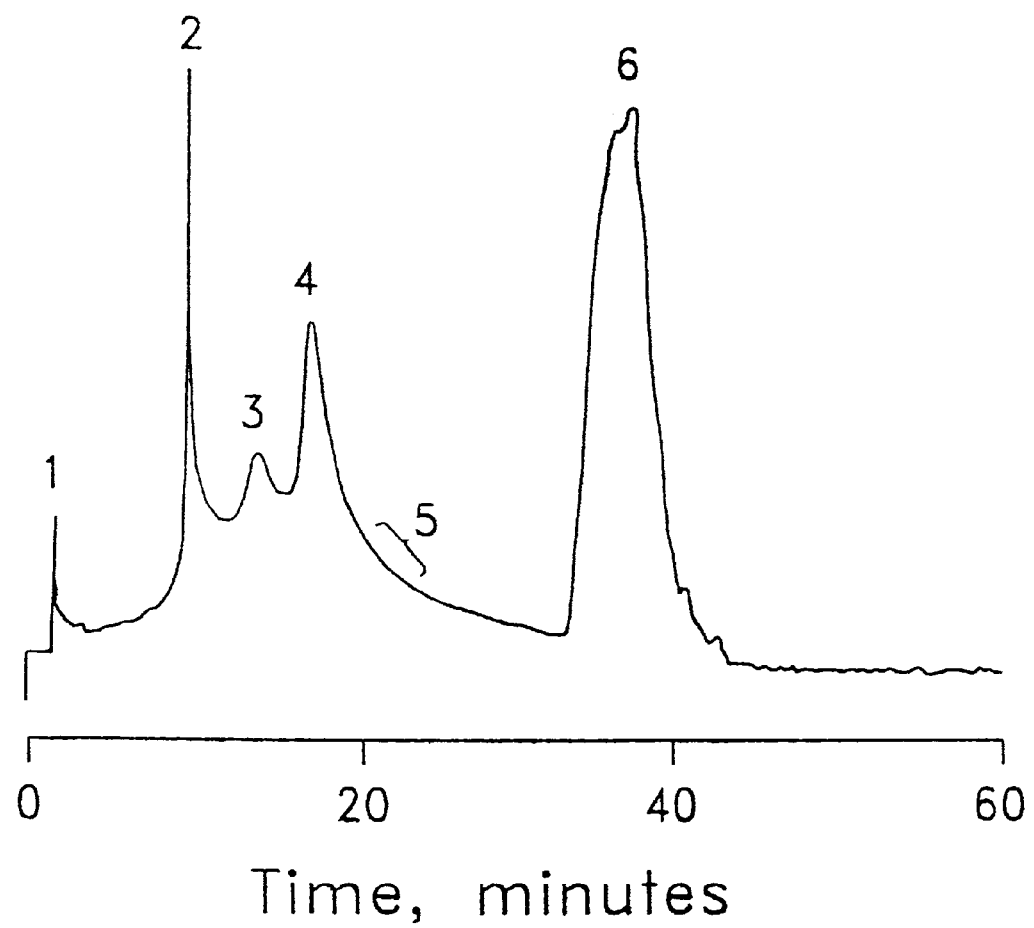
FIG. 2 shows a high-performance liquid chromatography (HPLC) trace obtained for a typical commercially-available natural-product humic acid.

The HPLC trace of the synthetic soil extract obtained in Example 10 is illustrated in FIG. 1. Peaks 1–6 were produced by this example. Peak 5 is under the shoulder of Peak 4 and is not overtly apparent. A mathematical first derivative of the detector signal versus time can more clearly show Peak 5. FIG. 2 shows the HPLC trace of a typical commercially-available natural humic acid. Peak 6 in FIGS. 1 and 2 was produced by a column wash with 90–100% v/v methanol and also contains synthetic humic acid. It can be seen that with the exception of the relative amounts of material in Peaks 2, 4, and 6, the remainder of the HPLC traces in FIGS. 1 and 2 are similar. Thus, the synthetic procedure of the preferred embodiments produced a humic acid material with physicochemical characteristics that are similar to those of a commercially available soil extract.

EXAMPLE 11

Preparation of Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid (1.68 grams, 10 mmoles) was dissolved in 300 milliliters of 0.1 N aqueous sodium hydroxide (NaOH). The solution pH was adjusted to 8.5 with 6 N HCl. Sodium periodate (0.75 gram, 3.5 mmoles) and sodium sulfide nonahydrate (0.24 gram, 1 millimole) was added, and the solution was placed in a water bath at 50° C. overnight. Boric acid (0.006 gram, 0.1 millimole), ferrous sulfate heptahydrate (0.28 gram, 1 millimole), and calcium sulfate dihydrate (0.17 gram, 0.1 millimole) were added and the solution was hours at room temperature. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.47 gram. The HPLC trace of the synthetic soil extract obtained in Example 11 was similar to that described in Example 10 and illustrated in FIG. 1.

EXAMPLE 12

Preparation of Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid (1.68 grams, 10 mmoles) was dissolved in 300 milliliters of 0.1 N aqueous sodium hydroxide (NaOH). The solution pH was adjusted to 8.5 with 6 N HCl. Sodium periodate (0.75 gram, 3.5 mmoles) and sodium sulfide nonahydrate (0.24 gram, 1 millimole) was added, and the solution was placed in a water bath at 50° C. overnight. gram, 1 millimole), and calcium sulfate dihydrate (0.17 gram, 0.1 millimole) were added and the solution stood quiescent overnight at 50° C. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.4 gram. The HPLC trace of the synthetic soil extract obtained in Example 12 was similar to that described in Example 10 and illustrated in FIG. 1.

EXAMPLE 13

Preparation of Synthetic Humic Acid from 3,4-Dihydroxycinnamic Acid (Caffeic Acid)

The starting organic compound is 3,4-dihydroxycinnamic acid (caffeic acid), shown in Table 1, represented by $R_1$=—$CHCHCO_2H$, $R_3,R_4$=—OH, and $R_2,R_5,R_6$=—H. Caffeic acid (1.8 grams, 10 mmoles) was dissolved in 300 milliliters of 0.1 N aqueous sodium hydroxide (NaOH). The remaining procedure followed that of the preceding Example. The yield of synthetic soil extract was 0.51 gram.

EXAMPLE 14

Preparation of a Synthetic Humic Acid from 1,3,4,5-Tetrahydroxycyclohexane-Carboxylic Acid 3-(3,4-Dihydroxycinnamate) (Chlorogenic Acid)

The starting organic compound is 1,3,4,5-tetrahydroxycyclohexane-carboxylic acid 3-(3,4-dihydroxycinnamate) (chlorogenic acid), shown in Table 2. Chlorogenic acid (3.54 grams, 10 mmoles) was dissolved in 300 milliliters of 0.1 N aqueous sodium hydroxide (NaOH). The remaining procedure followed that of the preceding Example. The yield of synthetic soil extract was 0.23 gram.

EXAMPLE 15

In Vitro Toxicity of Synthetic Humic Acid Prepared According to Examples 10, 11, and 12

Humic acid synthesized from homogentisic acid was prepared according to the procedure of Examples 10, 11 and 12. The in vitro toxicity of the materials was assessed as follows:

Five units of 450 milliliters each of whole human blood were collected into CP2D/AS-3 Leukotrap RC-PL systems. The blood was rested for 3 hours at room temperature. Each sample was weighed, and then centrifuged at 2820 revolutions per minute (2312 gravities) for 3 minutes, 44 seconds. The blood samples were then expressed through ATS-LPL filters into platelet storage bags. The filtration time was noted. The LR-PRP was centrifuged at 3600 revolutions per minute (3768 gravities) for 7 minutes. All but about 55 grams of platelet poor plasma was removed from each sample. The platelet concentrates were rested for 90 minutes at room temperature, and were then weighed and placed in a platelet incubator. RCM1 filters were primed with AS-3 solution. The primary bags were hung at a height of 60 inches above empty AS-3 bags, such that filtration occurred by gravity. The filtration time was noted, and the LRRCC systems were sealed off 3 inches below the RCM1 filters. Each RCM1 filter together with 6 inches of tubing and the LR-RCC, including the donor identification tube segment, were weighed. Samples were taken at this point for post-filtration testing (LR-RCC).

At Day 1, sufficient synthetic humic acid was added to each platelet concentrate so as to make its concentration 25 micrograms per milliliter. Treated platelet concentrates were then incubated in a platelet incubator for 1 hour, following which samples of each platelet concentrate were taken for testing. Subsequent samples were also taken on Day 5 for further testing.

Table 3 shows the effect of the synthetic humic acid prepared as described in Example 10 on the viability of platelet concentrates as measured according to the procedures of this Example. The results were all nominal, that is, the synthetic humic acid had no effect on platelet viability (i.e., is nontoxic). The same results were obtained when the concentration of humic acid was made 100 micrograms per milliliter instead of 25 micrograms per milliliter. These results are particularly noteworthy, as blood platelets are known to be sensitive to a variety of chemical agents. It is for this reason that few safe antiviral treatments are available for blood platelets.

TABLE 3

| Unit No. | pH at 22° C. | | $pCO_2$, mm Hg | | $pO_2$, mm Hg | | $HCO_3$, mmol/L | | MPV, fl | |
|---|---|---|---|---|---|---|---|---|---|---|
| | Day 1 | Day 5 | Day 1 | Day 5 | Day 1 | Day 5 | Day 1 | Day 5 | Day 1 | Day 5 |
| 1 | 7.466 | 7.394 | 19.3 | 12.8 | 33.5 | 44.4 | 16.8 | 9.5 | 7.0 | 6.6 |
| 2 | 7.321 | 7.215 | 21.6 | 14.3 | 9.9 | 22.2 | 13.8 | 7.3 | 6.7 | 6.3 |
| 3 | 7.320 | 7.276 | 24.4 | 16.6 | 10.3 | 21.3 | 15.6 | 9.7 | 6.7 | 6.5 |
| 4 | 7.368 | 7.308 | 20.7 | 14.3 | 13.4 | 22.2 | 14.6 | 8.9 | 6.5 | 6.3 |
| 5 | 7.457 | 7.454 | 20.1 | 13.8 | 23.7 | 29.0 | 17.1 | 11.6 | 7.7 | 7.4 |

TABLE 3-continued

| Unit No. | | | | | | | | | | |
|---|---|---|---|---|---|---|---|---|---|---|
| Mean | 7.386 | 7.329 | 21.2 | 14.4 | 18.2 | 27.8 | 15.6 | 9.4 | 6.9 | 6.6 |
| Std. Dev. | 0.071 | 0.095 | 2.0 | 1.4 | 10.2 | 9.8 | 1.4 | 1.5 | 0.5 | 0.6 |

| | WBC Yield, × $10^5$ | Platelet Yield, × $10^{10}$ | | Streaming | | % ESC | | % HSR | | Lactate, mmol/L | |
|---|---|---|---|---|---|---|---|---|---|---|---|
| Unit No. | Day 1 | Day 1 | Day 5 | Day 1 | Day 5 | Day 1 | Day 5 | Day 1 | Day 5 | Day 1 | Day 5 |
| 1 | 0.1 | 8.3 | 9.0 | 3 | 3 | 24.2 | 16.9 | 78.0 | 64.0 | 5.1 | 12.1 |
| 2 | 0.2 | 14.5 | 14.2 | 3 | 3 | 27.5 | 20.3 | 81.7 | 71.5 | 6.6 | 13.4 |
| 3 | 0.4 | 13.3 | 13.4 | 3 | 3 | 28.7 | 26.3 | 81.7 | 79.4 | 6.3 | 12.4 |
| 4 | 0.3 | 11.7 | 12.3 | 3 | 2 | 22.1 | 19.2 | 81.4 | 77.1 | 6.6 | 13.1 |
| 5 | 0.3 | 8.9 | 9.1 | 3 | 3 | 19.1 | 14.4 | 74.7 | 70.2 | 4.5 | 9.7 |
| Mean | 0.3 | 11.3 | 11.6 | 3.0 | 2.8 | 24.3 | 19.4 | 79.5 | 72.4 | 5.8 | 12.1 |
| Std. Dev. | 0.1 | 2.7 | 2.4 | 0.0 | 0.4 | 3.9 | 4.5 | 3.1 | 6.1 | 1.0 | 1.4 |

EXAMPLE 16

In Vitro Toxicity of Synthetic Humic Acid Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The in vitro toxicity of the materials was assessed as follows:

Cytotoxicity was examined with six concentrations of each humate material, and one "no-drug" concentration. All materials were tested in African green monkey kidney cells (CV-1; Diagnostic Hybrids, Inc., Athens, Ga.) in triplicate. The cells were provided in flat dishes containing multiple cell wells. The cells were cultured in the presence of different concentrations of humate materials for 24–36 hours at 35–37° C. in a $CO_2$-humidified incubator. The morphology of the cultured cells was examined visually to determine any cytotoxic effects. No abnormal cell morphology was observed in cultures with "no drug" nor in any containing humate concentrations up to 500 micrograms per milliliter. Furthermore, no apparent CV-1 cell death (that is, cell detachment from the bottom of the wells) was observed at any concentration of any material tested. The results established that the materials were not cytotoxic at concentrations up to at least 500 micrograms per milliliter.

EXAMPLE 17

In Vitro Toxicity Testing of Synthetic Humic Acid Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The in vitro toxicity of the materials was assessed as follows:

The Neutral Red method of assaying for humate toxicity was carried out in roughly the same manner for all cell lines tested; that employed for human foreskin fibroblast (HFF) cells is provided as a representative example. Twenty-four hours prior to assay, HFF cells were plated into 96-well plates at a concentration of 2.5×104 cells per well. After 24 hours, the medium was aspirated and 125 microliters of medium+humate was added to the first row of wells and then diluted serially 1:5 using the Cetus Liquid Handling System. After humate addition, the plates were incubated for seven days in a $CO_2$ incubator at 37° C. At this time the medium+humate was aspirated and 200 microliters per well of 0.01% neutral red in PBS was added. This was incubated in the $CO_2$ incubator for 1 hour. The dye was aspirated and the cells were washed using a Nunc Plate Washer. After removing the PBS, 200 micrograms per well of 50% EtOH/1% glacial acetic acid (in $H_2O$) was added. The plates were rotated for 15 minutes and the optical densities were read at 540 nanometers on a plate reader.

Visual observation was employed to confirm cell toxicity. Wells of uninfected cells treated with each concentration of test compound were used. The cells were examined microscopically for any changes in appearance compared to normal control cells run in the same plate. These changes became manifest as enlargement, granularity, cells with ragged edges, a filmy appearance, rounding, detachment from the surface of the well, or other changes. The changes were given a designation of T (100% toxic), PVH (partially toxic-very heavy—80%), PH (partially toxic-heavy—60%), P partially toxic—40%), Ps (partially toxic-slight—20%), or 0 (no toxicity—0%), conforming to the degree of cytotoxicity seen. A 50% cytotoxic concentration ($TC_{50}$) was determined by regression analysis of these data.

All humates evaluated were not cytotoxic at levels at least as high as 100 micrograms per milliliter, as shown below in Table 4. Visual observation of caffeic acid and natural-product humates with uninfected MDCK cells in toxicity control wells appeared initially to indicate drug toxicity. However, the humates were not in fact toxic as revealed by Neutral Red assays. Rather, the humate compounds were found to bind to cell surfaces, thereby changing their color and giving them an exanimate appearance. This discoloration was also observed in a concentration-dependent manner at levels where antiviral activity was present.

TABLE 4

| | $TC_{50}$ | | | | | |
|---|---|---|---|---|---|---|
| | | | | | LLC-$MK_2$[5] | |
| Compound[1] | BSC-1[2] | HFF[3] | MDCK[4] | Trial 1 | Trial 2a[7] | Trial 2b[8] |
| Caffeic Acid Humate | >100 | >100 | >100 | >100 | >1000 | >1000 |

TABLE 4-continued

| | | | | TC$_{50}$ | | |
|---|---|---|---|---|---|---|
| | | | | | LLC-MK$_2$[5] | |
| Compound[1] | BSC-1[2] | HFF[3] | MDCK[4] | Trial 1 | Trial 2a[7] | Trial 2b[8] |
| Chlorogenic Acid Humate | >100 | >100 | —[6] | —[6] | >1000 | >1000 |
| Homogentisic Acid Humate | >100 | >100 | >100 | >100 | >1000 | >1000 |
| Natural-Product Humate | >100 | >100 | —[6] | —[6] | 700 | >1000 |

[1]All concentrations in micrograms per milliliter.
[2]African green monkey kidney cells.
[3]Human foreskin fibroblast cells.
[4]Madin Darby canine kidney cells.
[5]Adult rhesus monkey kidney cells.
[6]Not evaluated.
[7]Neutral Red assay.
[8]Visual assay.

EXAMPLE 18

Cell Proliferation (Viability) Testing of Synthetic Humic Acid Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14.

The in vitro toxicity of the materials in terms of cell proliferation (viability) was assessed in the following procedure. The counting method of assaying for cell proliferation (viability) was carried out in roughly the same manner for all cell lines tested; that employed for HFF cells is provided as a representative example. Twenty-four hours prior to assay, HFF cells were seeded in 6-well plates at a concentration of $2.5 \times 10^4$ cells per well in minimum essential medium (MEM) containing 10% fetal bovine serum (FBS). On the day of the assay, humates were diluted serially in MEM containing 10% FBS at increments of 1:5 covering a range from 100 to 0.03 micrograms per milliliter. The medium from the wells was then aspirated and 2 milliliters of each humate concentration was then added to each well. The cells were then incubated in a $CO_2$ incubator at 37° C. for 72 hours. At the end of this time, the medium+humate solution was removed and the cells washed. One milliliter of 0.25% trypsin was added to each well and incubated until the cells started to come off of the plate. The cell-medium mixture was then pipetted up and down vigorously to break up the cell suspension and 0.2 milliliter of the mixture was added to 9.8 milliliters of Isoton III and counted using a Coulter Counter. Each sample was counted three times with two replicate wells per sample.

All humates except for caffeic acid humate with Daudi cells (Burkitt's lymphoma derived cells) did not inhibit 50% cell proliferation (CP$_{50}$) at drug levels at least as a high as 50 micrograms per milliliter, as shown below in Table 5.

TABLE 5

| | CP$_{50}$, μg/mL | |
|---|---|---|
| Compound[1] | HFF[2] | Daudi[3] |
| Caffeic Acid Humate | 71.2 | <0.08 |
| Chlorogenic Acid Humate | 96 | >50 |
| Homogentisic Acid Humate | 88.4 | >50 |
| Natural-Product Humate | >100 | >50 |

[1]All concentrations in micrograms per milliliter.
[2]Human foreskin fibroblast cells.
[3]Burkitt's lymphoma derived cells.

EXAMPLE 19

In Vivo Toxicity of Synthetic Humic Acid Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14.

The in vivo acute intravenous systemic toxicity of the humate materials was assessed as follows. Each humate material was dissolved separately in sterile, pyrogen-free 0.9% aqueous sodium chloride solvent to yield solutions of final concentrations of 1, 0.5 and 0.25 milligrams per milliliter. The test animals were viral antibody-free Swiss Webster mice, which weighed in the range of 17–23 grams at the time of testing. All test animals were quarantined and checked for signs of disease prior to testing. All test animals were group-housed five per cage in plastic cages with stainless steel suspended lids. For each dose of each humate material, ten mice (five males and five females) were administered the sample humate material intravenously in the amount of 50 milliliters per kilogram body weight. Ten additional mice were similarly administered 0.9% sodium chloride solution (the solvent vehicle) as a zero control. This procedure resulted in humate doses of 50 milligrams per kilogram body weight from the 1 milligram per milliliter solution, 25 milligrams per kilogram from the 0.5 milligram per milliliter solution, 12.5 milligrams per kilogram from the 0.25 milligram per milliliter solution, and 0 milligrams per kilogram from the 0.9% sodium chloride (blank) solution. Following injection, the mice were offered a balanced Teklad diet and water ad libitum for the duration of the study. All mice were examined for viability for fourteen days. Zero time, Day seven and Day fourteen weights and toxic symptoms were recorded. No mortalities were observed for any of the mice over the fourteen day observation period and, while some clinical findings were observed, they were not indicative of toxicity.

EXAMPLE 20

Hemorrhagic Fever Cytoprotection Properties of Natural-Product and Synthetic Humic Acids Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The anti-viral properties of the humate materials were assessed according to the following methods:

Pichinde hemorrhagic fever virus 4763 was obtained from the Center for Disease Control (CDC). The test cell line consisted of African green monkey kidney cells (BSC-1). Ribavirin was the reference drug.

The first protocol used to determine the cytoprotection properties of the humate materials was as follows: each test was run in 96-well flat-bottomed microplates. Four $\log_{10}$ dilutions of each test compound were added to 3 cups containing the cell monolayer. Within 5 minutes the virus was added and the plate sealed, incubated at 37° C., and the drug inhibition of the viral cytopathic effect (CPE) assessed microscopically when untreated infected controls had developed a 3 to 4+ CPE (approximately 72 to 120 hours). The data were expressed as 50% effective inhibitory concentration (CPE $EC_{50}$).

The second cytoprotection assay protocol, employed to validate the CPE results, was as follows: in the neutral red dye uptake version of the antiviral test protocol described immediately above, the same 96-well microplates were utilized after the CPE had been read. Neutral red dye was then added to the medium: cells not damaged by virus take up a greater amount of dye, which can be read on a computerized micro plate autoreader (the method is described in detail by McManus: *Appl. Environ. Microbiol.* 1976, 31, 35–38). The data were expressed as 50% effective inhibitory concentration (NR $EC_{50}$).

The results of drug efficacy testing against Pichinde hemorrhagic fever virus with the above-described protocols are summarized in Table 6.

This Example demonstrates that the synthetic humate materials can protect cells against infection by Pichinde hemorrhagic fever virus.

TABLE 6

| Compound[1] | CPE $EC_{50}$ | NR $EC_{99}$ |
|---|---|---|
| Caffeic Acid Humate | <1 | <1 |
| Chlorogenic Acid Humate | <1 | <1 |
| Homogentisic Acid Humate | <1 | <1 |
| Natural-Product Humate | <1 | <1 |
| Ribavirin | 0.3 | <1 |

[1]All concentrations in micrograms per milliliter.

EXAMPLE 21

Punta Toro A Hemorrhagic Fever Cytoprotection Properties of Natural-Product and Synthetic Humic Acids Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The anti-viral properties of the humate materials were assessed according to the following methods:

Punta Toro A hemorrhagic fever virus type Adames was obtained from the Center for Disease Control (CDC). The test cell line consisted of adult Rhesus monkey kidney cells (LLC-MK$_2$).

The two protocols used to determine the cytoprotection properties of the humate materials were as described in Example 20.

The results of drug efficacy testing against Punta Toro A hemorrhagic fever virus with the above-described protocols are summarized in Table 7.

This Example demonstrates that the synthetic humate materials can protect cells against infection by Punta Toro A hemorrhagic fever virus.

TABLE 7

| Compound[1] | CPE $EC_{50}$ | NR $EC_{99}$ |
|---|---|---|
| Caffeic Acid Humate | 5 | 27 |
| Chlorogenic Acid Humate | 10 | 100 |
| Homogentisic Acid Humate | 5 | 15 |
| Natural-Product Humate | 10 | 15 |
| Ribavirin | 5 | 5 |

[1]All concentrations in micrograms per milliliter.

EXAMPLE 22

Punta Toro A Hemorrhagic Fever Time-of-Addition Cytoprotection Properties of Natural-Product and Synthetic Humic Acids Prepared According to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The anti-viral properties of the humate materials were assessed according to the following methods:

Punta Toro A hemorrhagic fever virus type Adames was obtained from the Center for Disease Control (CDC). The test cell line consisted of a dult Rhesus monkey kidney cells (LLC-MK$_2$).

The two protocols used to determine the cytoprotection properties of the humate materials were as described in Example 20, except that drugs were added at specific times to the test wells containing virus.

The results of drug efficacy testing against Punta Toro A hemorrhagic fever virus with the above-described protocols are summarized in Table 8.

This Example confirms that the synthetic humate materials can protect cells against infection by Punta Toro A hemorrhagic fever virus.

TABLE 8

| Time of Addition, hours | $EC_{50}$, CPE-NR Methods[1] | | |
|---|---|---|---|
| | Caffeic Acid Humate | Natural-Product Humate | Ribavirin |
| −1 | 25–100 | 30–50 | 10–6 |
| 0 | 10–3 | 30–7 | 4–3 |
| 1 | 25–40 | 30–30 | 4–5 |
| 2 | 39–75 | 30–60 | 8–5 |
| 4 | 80–>100 | 100–>100 | 4–9 |
| 6 | 80–100 | 100–50 | 10–8 |
| 8 | >100–>100 | >100–>100 | 8–10 |

TABLE 8-continued

| Time of Addition, hours | EC$_{50}$, CPE-NR Methods[1] | | |
|---|---|---|---|
| | Caffeic Acid Humate | Natural-Product Humate | Ribavirin |
| 12 | >100->100 | >100->100 | 8–12 |
| 24 | >100->100 | >100->100 | 2–35 |

[1]All concentrations in micrograms per milliliter.

The Examples described above establish relevant hemorrhagic fever antiviral data and efficacy of the synthetic humate compounds. The studies conform to current requirements put forth by the FDA for preclinical analysis of new anti-virals.

Pharmaceutical Compositions

Pharmaceutical compositions comprising compounds according to preferred embodiments can be administered by mouth in the form of tablets, capsules, solutions, emulsions, or suspensions; by inhalation, in the form of liquid, solid particles, or a spray; by absorption through the skin, by an appliance such as a transdermal patch; or by way rectum, in the form of suppositories. Administration can also take place parenterally, for example in the form of injectable solutions.

Tablets are prepared by mixing the Active Ingredient ("Active Ingredient" is one or more compounds inclusive of synthetic phenolic polymeric materials obtained by the methods of the preferred embodiments) with pharmaceutically inert, inorganic or organic carriers, diluents, and/or excipients. Examples of such excipients which can be used for tablets, include lactose, maize starch or derivatives thereof, talc, stearic acid or salts thereof. Examples of suitable excipients for soft gelatin capsules include vegetable oils, waxes, fats, semisolid and liquid polyols.

Suitable excipients for the preparation of solutions and syrups include water, polyols, sucrose, invert sugar and glucose.

Suitable excipients for injectable solutions include water, alcohols, polyols, glycerol, and vegetable oils.

These pharmaceutical compositions can additionally contain preservatives, solubilizers, stabilizers, wetting agents, emulsifiers, sweeteners, colorants, flavorings, buffers, coating agents and antioxidants.

Pharmaceutical compositions according to preferred embodiments to be administered by parenteral injection comprise pharmaceutically acceptable, preferably sterile aqueous or nonaqueous solutions, dispersions, suspensions or emulsions as well as sterile powders for reconstitution into sterile injectable solutions or dispersions just prior to use.

The active ingredient can also be made in microencapsulated form.

Method of Treatment

In accordance with one preferred embodiment, the compounds and pharmaceutical compositions may be used in the prophylaxis and/or treatment of disease or conditions in mammals, including humans. Such diseases or conditions include those effected by hemorrhagic fever viruses. Methods of use include the step of administering a therapeutically effective amount of the active ingredient to a mammal in need thereof.

Preferably, the compounds of preferred embodiments are administered in the form of a pharmaceutical formulation. Thus, the compounds may be administered orally, parenterally, topically, rectally and etc., in appropriate dosage units, as desired.

The term parenteral as used herein includes subcutaneous, intravenous, intraarterial, injection or infusion techniques, without limitation. The term, "topically" emcompasses administration rectally and by inhalation spray, as well as the more common routes of the skin and the mucous membranes of the mouth and nose.

Actual dosage levels of active ingredients in the pharmaceutical compositions may be varied so as to administer an amount of the active compound(s) that is effective to achieve the desired therapeutic response for a particular patient.

The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

Many modifications and variations of the embodiments described herein may be made without departing from the scope, as is apparent to those skilled in the art. The specific embodiments described herein are offered by way of example only.

What is claimed is:

1. A method for protecting against and/or treating hemorrhagic fever virus infections in a mammal comprising administering to the mammal effective amount of a synthetic phenolic polymeric material, said synthetic phenolic material having been prepared by the following steps:

a) dissolving in an aqueous solution at least one starting organic compound comprising at least one hydroxyl group and at least one carbonyl group or at least two hydroxyl groups on an aromatic structure;

b) oxidizing and polymerizing the at least one starting organic compound;

c) adding at least one water soluble compound or salt selected from the group consisting of boric acid, borate salts, alkaline earth salts, transition metal salts, alkaline sulfides, alkaline earth sulfides, or transition metal sulfides to the aqueous solution resulting from step b);

d) allowing the aqueous solution from step c) to stand with or without stirring at about 20° C. to 100° C. for at least about 2 hours; and e) removing molecules from the solution resulting from step d) below about 500 to about 10,000 daltons.

2. The method according to claim 1, wherein the starting organic compound is selected from the group consisting of a compound represented by the Formula I:

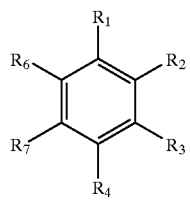

(I)

wherein $R_1, R_2, R_3, R_4, R_5$, and $R_6$ is a substituent selected from the group consisting of H, $CH_3$, $CH_2CH_3$, $(CH_2)_2CH_3$, $CH(CH_3)_2$, OH, $OCH_3$, CHO, $CO_2H$, $CO_2CH_3$, $CH_2OH$, $CH_2OCH_3$, $CH_2CHO$, $CH_2CO_2H$, $CH_2CO_2CH_3$, $(CH_2)_2OH$, $(CH_2)_2OCH_3$, $(CH_2)_2CHO$, $(CH_2)_2CO_2H$, $(CH_2)_2CO_2CH_3$, $CH(CH_3)OH$, $CH(CH_3)OCH_3$, $CH(CH_3)CHO$, $CH(CH_3)CO_2H$, $CH(CH_3)CO_2CH_3$, $CH(CH_3)CH_2OH$, $CH(CH_3)CH_2OCH_3$, $CH(CH_3)CH_2CHO$, $CH(CH_3)CH_2CO_2H$, $CH(CH_3)CH_2CO_2CH_3$, $CH(OH)_2$, $CH(OH)OCH_3$, $CH(OH)CHO$, $CH(OH)CO_2H$, $CH(OH)CO_2CH_3$, $CH(OCH_3)OH$, $CH(OCH_3)_2$, $CH(OCH_3)CHO$, $CH(OCH_3)CO_2H$, $CH(OCH_3)CO_2CH_3$, $CH(OH)CH_2OH$, $CH(OH)CH_2OCH_3$, $CH(OH)CH_2CHO$, $CH(OH)CH_2CO_2H$, $CH(OH)CH_2CO_2CH_3$, $CH(OCH_3)CH_2OH$, $CH(OCH_3)CH_2OCH_3$, $CH(OCH_3)CH_2CHO$, $CH(OCH_3)CH_2CO_2H$, $CH(OCH_3)CH_2CO_2CH_3$, $(CH_2)_3OH$, $(CH_2)_3OCH_3$, $(CH_2)_3CHO$, $(CH_2)_3CO_2H$, $(CH_2)_3CO_2CH_3$, CHCHOH (cis or trans), $CHCHOCH_3$ (cis or trans), CHCHCHO (cis or trans), $CHCHCO_2H$ (cis or trans), $CHCHCO_2CH_3$ (cis or trans), $CH_2CHCHOH$ (cis or trans), $CH_2CHCHOCH_3$ (cis or trans), $CH_2CHCHCHO$ (cis or trans), $CH_2CHCHCO_2H$ (cis or trans), and $CH_2CHCHCO_2CH_3$ (cis or trans).

3. The method according to claim 2, wherein the starting organic compound comprises at least one hydroxyl group and at least one carboxylic acid group.

4. The method according to claim 1, wherein the starting organic compound is selected from the group consisting of

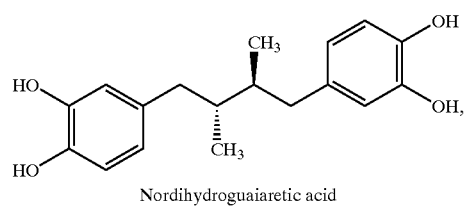

Nordihydroguaiaretic acid

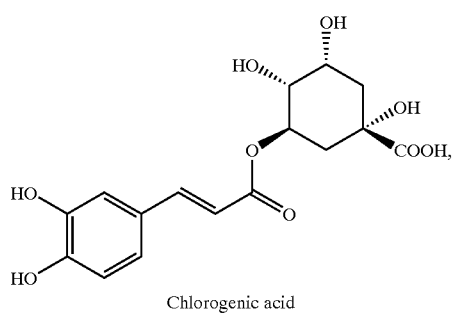

Chlorogenic acid

-continued

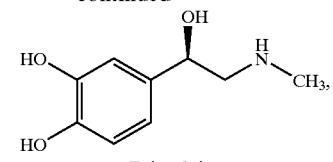

Epinephrine

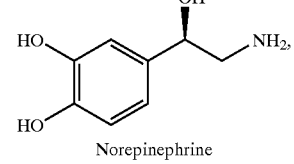

Norepinephrine

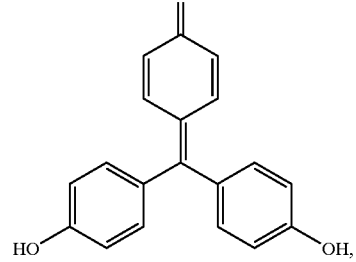

Aurin

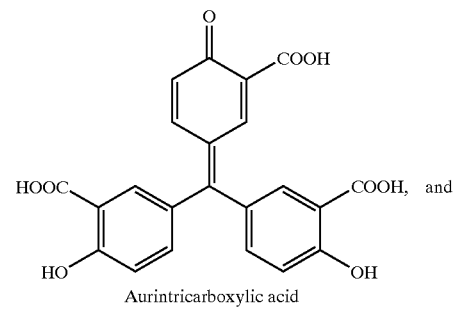

Aurintricarboxylic acid, and

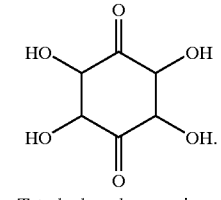

Tetrahydroxybenzoquinone

5. The method according to claim 1, wherein the aqueous solution in step a) comprises sodium hydroxide.

6. The method according to claim 1, wherein step b) comprises:
  b1) adjusting the pH of the aqueous solution resulting from step a) to between about 8 and 11;
  b2) adding an alkaline periodate salt or alkaline-earth periodate salt to the aqueous solution resulting from step b1); and
  b3) maintaining the temperature of the solution from step b2) between about 20° C. and 100° C. for a period of at least about 30 minutes.

7. The method according to claim 6, wherein the temperature in step b3) is between about 35° C. and 80° C.

8. The method according to claim 1, wherein the synthetic phenolic polymeric material has been prepared by a method that further comprises a step, following step e), of:
  concentrating the solution resulting from step e).

9. The method according to claim 8, wherein the method of preparation of the synthetic phenolic polymeric material further comprises a step, following step f), of:

g) removing the water from the solution resulting from the step f).

10. The method according to claim 1, wherein the temperature in step d) is between about 20° C. and 80° C.

11. The method according to claim 1, wherein the hemorrhagic fever virus infection is effected by arenaviridae.

12. The method according to claim 11, wherein the hemorrhagic fever virus infection is effected by lymphocytic choriomeningitis virus, Lassa virus, Junin virus, Machupo virus, Guanarito virus, Sabia virus, or Pichinde virus.

13. The method according to claim 1, wherein the hemorrhagic fever virus infection is effected by filoviridae.

14. The method according to claim 13, wherein the hemorrhagic fever virus infection is effected by Ebola virus or Marburg virus.

15. The method according to claim 1, wherein the hemorrhagic fever virus infection is effected by bunyaviridae.

16. The method according to claim 15, wherein the hemorrhagic fever virus infection is effected by Punta Toro virus, Rift Valley fever virus, Crimean-Congo hemorrhagic fever virus, and Hataan virus.

17. The method according to claim 1, wherein the hemorrhagic fever virus infection is effected by flaviviridae.

18. The method according to claim 17, wherein the hemorrhagic fever virus infection is effected by yellow fever virus, dengue virus, Omsk hemorrhagic fever virus, or Kyansanur forest disease virus.

19. The method according to claim 1, wherein the mammal is a human.

20. The method according to claim 1, wherein administering the effective amount of synthetic phenolic polymeric material is performed systemically.

21. The method according to claim 1, wherein administering the effective amount of synthetic phenolic polymeric material is performed topically.

22. The method according to claim 1, further comprising administering an additional antiviral composition in combination with the effective amount of a synthetic phenolic polymeric material.

23. The method according to claim 22, wherein administering the effective amount of synthetic phenolic polymeric material and the antiviral composition is performed systemically.

24. The method according to claim 22, wherein administering the effective amount of synthetic phenolic polymeric material and the antiviral composition is performed topically.

25. A method of inhibiting hemorrhagic fever viral attachment to host cells in a mammal comprising administering to the mammal an effective amount of a synthetic phenolic polymeric material, said synthetic phenolic material having been prepared by the following steps:
  a) dissolving in an aqueous solution at least one starting organic compound comprising at least one hydroxyl group and at least one carbonyl group or at least two hydroxyl groups on an aromatic structure;
  b) oxidizing and polymerizing the at least one sing organic compound;
  c) adding at least one water soluble compound or salt selected from the group consisting of boric acid, borate salts, alkaline earth salts, transition metal salts, alkaline sulfides, alkaline earth sulfides, or transition metal sulfides to the aqueous solution resulting from step b);
  d) allowing the aqueous solution from step c) to stand with or without stirring at about 20° C. to 100° C. for at least about 2 hours; and
  e) removing molecules from the solution resulting from step d) below about 500 to about 10,000 daltons.

26. The method according to claim 25, wherein the starting organic compound is selected from the group consisting of a compound represented by the formula I:

(I)

wherein $R_1, R_2, R_3, R_4, R_5$, and $R_6$ is a substituent selected from the group consisting of H, $CH_3$, $CH_2CH_3$, $(CH_2)_2CH_3$, $CH(CH_3)_2$, OH, $OCH_3$, CHO, $CO_2H$, $CO_2CH_3$, $CH_2OH$, $CH_2OCH_3$, $CH_2CHO$, $CH_2CO_2H$, $CH_2CO_2CH_3$, $(CH_2)_2OH$, $(CH_2)_2OCH_3$, $(CH_2)_2CHO$, $(CH_2)_2CO_2H$, $(CH_2)_2CO_2CH_3$, $CH(CH_3)OH$, $CH(CH_3)OCH_3$, $CH(CH_3)CHO$, $CH(CH_3)CO_2H$, $CH(CH_3)CO_2CH_3$, $CH(CH_3)CH_2OH$, $CH(CH_3)CH_2OCH_3$, $CH(CH_3)CH_2CHO$, $CH(CH_3)CH_2CO_2H$, $CH(CH_3)CH_2CO_2CH_3$, $CH(OH)_2$, $CH(OH)OCH_3$, $CH(OH)CHO$, $CH(OH)CO_2H$, $CH(OH)CO_2CH_3$, $CH(OCH_3)OH$, $CH(OCH_3)_2$, $CH(OCH_3)CHO$, $CH(OCH_3)CO_2H$, $CH(OCH_3)CO_2CH_3$, $CH(OH)CH_2OH$, $CH(OH)CH_2OCH_3$, $CH(OH)CH_2CHO$, $CH(OH)CH_2CO_2H$, $CH(OH)CH_2CO_2CH_3$, $CH(OCH_3)CH_2OH$, $CH(OCH_3)CH_2OCH_3$, $CH(OCH_3)CH_2CHO$, $CH(OCH_3)CH_2CO_2H$, $CH(OCH_3)CH_2CO_2CH_3$, $(CH_2)_3OH$, —$(CH_2)_3OCH_3$, $(CH_2)_3CHO$, $(CH_2)_3CO_2H$, $(CH_2)_3CO_2CH_3$, CHCHOH (cis or trans), $CHCHOCH_3$ (cis or trans), CHCHCHO (cis or trans), $CHCHCO_2H$ (cis or trans), $CHCHCO_2CH_3$ (cis or trans), $CH_2CHCHOH$ (cis or trans), $CH_2CHCHOCH_3$ (cis or trans), $CH_2CHCHCHO$ (cis or trans), $CH_2CHCHCO_2H$ (cis or trans), and $CH_2CHCHCO_2CH_3$ (cis or trans).

27. The method according to claim 26, wherein the starting organic compound comprises at least one hydroxyl group and at least one carboxylic acid group.

28. The method according to claim 25, wherein the starting organic compound is selected from the group consisting of Nordihydroguaiaretic acid Chlorogenic acid

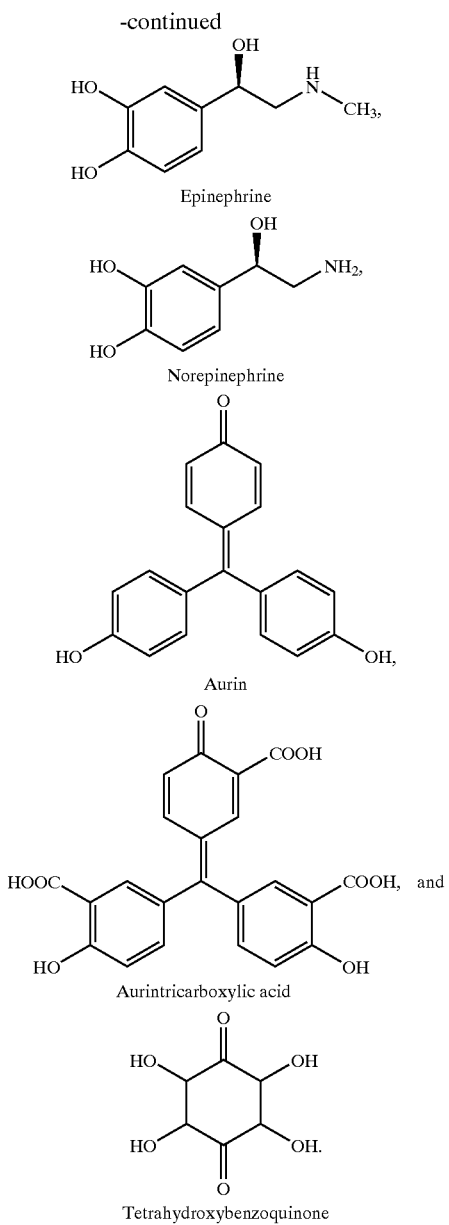

29. The method according to claim 25, wherein the aqueous solution in step a) comprises sodium hydroxide.

30. The method according to claim 25, wherein step b) comprises:
   b1) adjusting the pH of the aqueous solution resulting from step a) to between about 8 and 11;
   b2) adding an alkaline periodate salt or alkaline-earth periodate salt to the aqueous solution resulting from step b1); and
   b3) maintaining the temperature of the solution from step b2) between about 20° C. and 100° C. for a period of at least about 30 minutes.

31. The method according to claim 30, wherein the temperature in step b3) is between about 35° C. and 80° C.

32. The method according to claim 25, wherein the synthetic phenolic polymeric material has been prepared by a method that further comprises a step, following step e), of:
   f) concentrating the solution resulting from step e).

33. The method according to claim 32, wherein the method of preparation of the synthetic phenolic polymeric material further comprises a step, following step f), of:
   g) removing the water from the solution resulting the step f).

34. The method according to claim 25, wherein the temperature in step d) is between about 35° C. and 80° C.

35. The method according to claim 25, wherein the hemorrhagic fever virus infection is effected by arenaviridae.

36. The method according to claim 35, wherein the hemorrhagic fever virus infection is effected by lymphocytic choriomeningitis virus, Lassa virus, Junin virus, Machupo virus, Guanarito virus, Sabia virus, or Pichinde virus.

37. The method according to claim 25, wherein the hemorrhagic fever virus infection is effected by filoviridae.

38. The method according to claim 37, wherein the hemorrhagic fever virus infection is effected by Ebola virus or Marburg virus.

39. The method according to claim 25, wherein the hemorrhagic fever virus infection is effected by bunyaviridae.

40. The method according to claim 39, wherein the hemorrhagic fever virus infection is effected by Punta Toro virus, Rift Valley fever virus, Crimean-Congo hemorrhagic fever virus, and Hataan virus.

41. The method according to claim 25, wherein the hemorrhagic fever virus infection is effected by flaviviridae.

42. The method according to claim 41, wherein the hemorrhagic fever virus infection is effected by yellow fever virus, dengue virus, Omsk hemorrhagic fever virus, or Kyansanur forest disease virus.

43. The method according to claim 25, wherein the mammal is a human.

44. The method according to claim 25, wherein administering the effective amount of synthetic phenolic polymeric material is performed systemically.

45. The method according to claim 25, wherein administering the effective amount of synthetic phenolic polymeric material is performed topically.

46. The method according to claim 25, further comprising administering an additional antiviral composition in combination with the effective amount of a synthetic phenolic polymeric material.

47. The method according to claim 46, wherein administering the effective amount of synthetic phenolic polymeric material and the antiviral composition is performed systemically.

48. The method according to claim 46, wherein administering the effective amount of synthetic phenolic polymeric material and the antiviral composition is performed topically.

* * * * *

UNITED STATES PATENT AND TRADEMARK OFFICE
CERTIFICATE OF CORRECTION

PATENT NO.    : 6,524,567 B2
DATED         : February 25, 2003
INVENTOR(S)   : Richard J. Laub It is certified that error appears in the above-identified patent and that said Letters Patent is hereby corrected as shown below:

<u>Column 28,</u>
Line 43, insert -- an -- between "mammal" and "effective"

<u>Column 31,</u>
Line 56, delete "sing" and insert -- starting --

Signed and Sealed this

Ninth Day of December, 2003

JAMES E. ROGAN
*Director of the United States Patent and Trademark Office*